(12) United States Patent
Sacolick et al.

(10) Patent No.: US 11,510,588 B2
(45) Date of Patent: Nov. 29, 2022

(54) TECHNIQUES FOR NOISE SUPPRESSION IN AN ENVIRONMENT OF A MAGNETIC RESONANCE IMAGING SYSTEM

(71) Applicant: Hyperfine Operations, Inc., Guilford, CT (US)

(72) Inventors: Laura Sacolick, Guilford, CT (US); Hadrien A. Dyvorne, New York, NY (US)

(73) Assignee: Hyperfine Operations, Inc., Guilford, CT (US)

( * ) Notice: Subject to any disclaimer, the term of this patent is extended or adjusted under 35 U.S.C. 154(b) by 83 days.

(21) Appl. No.: 16/952,317

(22) Filed: Nov. 19, 2020

(65) Prior Publication Data

US 2021/0153765 A1 May 27, 2021

Related U.S. Application Data

(60) Provisional application No. 62/941,940, filed on Nov. 29, 2019, provisional application No. 62/941,369, filed on Nov. 27, 2019.

(51) Int. Cl.
*G01R 33/58* (2006.01)
*A61B 5/055* (2006.01)
(Continued)

(52) U.S. Cl.
CPC .......... *A61B 5/055* (2013.01); *G01R 33/3854* (2013.01); *G01R 33/445* (2013.01); *G01R 33/4818* (2013.01); *G01R 33/583* (2013.01)

(58) Field of Classification Search
CPC ................ A61B 5/055; G01R 33/3854; G01R 33/445; G01R 33/4818; G01R 33/583
See application file for complete search history.

(56) References Cited

U.S. PATENT DOCUMENTS

| 4,661,775 A | 4/1987 | Kormos et al. |
| 4,885,542 A | 12/1989 | Yao et al. |

(Continued)

FOREIGN PATENT DOCUMENTS

| CN | 102414572 A | 4/2012 |
| CN | 106164694 A | 11/2016 |

(Continued)

OTHER PUBLICATIONS

U.S. Appl. No. 14/938,430, filed Nov. 11, 2015, Sacolick et al.

(Continued)

*Primary Examiner* — G. M. A. Hyder
(74) *Attorney, Agent, or Firm* — Wolf, Greenfield & Sacks, P.C.

(57) ABSTRACT

Techniques for suppressing noise in an environment of a magnetic resonance (MR) imaging system having at least one primary coil and at least one auxiliary sensor. The techniques involve estimating a transform, that, when applied to noise received by the at least one auxiliary sensor, provides an estimate of noise received by the at least one primary coil. The transform is estimated from data obtained by the at least one primary coil and the least one auxiliary sensor, with the data being weighted prior to estimation to remove or suppress data in regions with a high signal to noise ratio. In turn, the estimated transform may be applied to noise measured by the at least one auxiliary sensor during imaging of a patient, to estimate and suppress noise present in the MR signals received by the at least one primary coil during imaging.

20 Claims, 9 Drawing Sheets

(51) Int. Cl.
  *G01R 33/385* (2006.01)
  *G01R 33/44* (2006.01)
  *G01R 33/48* (2006.01)

(56) References Cited

U.S. PATENT DOCUMENTS

| | | | |
|---|---|---|---|
| 4,893,082 A | 1/1990 | Letcher |
| 4,978,919 A | 12/1990 | Hinks |
| 5,227,723 A | 7/1993 | Sepponen |
| 5,245,286 A | 9/1993 | Carlson et al. |
| 5,291,137 A | 3/1994 | Freedman |
| 5,629,624 A | 5/1997 | Carlson et al. |
| 5,655,533 A | 8/1997 | Petropoulos et al. |
| 5,814,987 A | 9/1998 | Smith et al. |
| 6,037,850 A | 3/2000 | Honmei et al. |
| 6,201,987 B1 | 3/2001 | Dumoulin |
| 6,211,677 B1 | 4/2001 | Burl et al. |
| 6,242,919 B1 | 6/2001 | Zuk et al. |
| 6,317,618 B1 | 11/2001 | Livni et al. |
| 6,424,152 B1 | 7/2002 | Prins et al. |
| 6,445,184 B1 | 9/2002 | Tanttu |
| 6,448,773 B1 | 9/2002 | Zhang |
| 6,504,373 B2 | 1/2003 | Tsuda |
| 6,624,630 B1 | 9/2003 | Foxall |
| 6,844,732 B2 | 1/2005 | Carlini et al. |
| 6,845,262 B2 | 1/2005 | Albert et al. |
| 7,116,105 B1 | 10/2006 | Zhang |
| 7,126,333 B2 | 10/2006 | Beard et al. |
| 7,504,825 B2 | 3/2009 | Pittaluga et al. |
| 8,203,341 B2 | 6/2012 | Teklemariam et al. |
| 8,232,799 B2 | 7/2012 | Hajian et al. |
| 8,334,695 B2 | 12/2012 | McColl et al. |
| 8,816,684 B2 | 8/2014 | Walsh |
| 8,890,527 B1 | 11/2014 | Balcom et al. |
| 8,970,217 B1 | 3/2015 | Kadin |
| 9,541,616 B2 | 1/2017 | Rothberg et al. |
| 9,547,057 B2 | 1/2017 | Rearick et al. |
| 9,625,543 B2 | 4/2017 | Rearick et al. |
| 9,625,544 B2 | 4/2017 | Poole et al. |
| 9,638,773 B2 | 5/2017 | Poole et al. |
| 9,645,210 B2 | 5/2017 | McNulty et al. |
| 9,702,946 B1 | 7/2017 | Kovtunov et al. |
| 9,797,971 B2 | 10/2017 | Rearick et al. |
| 9,817,093 B2 | 11/2017 | Rothberg et al. |
| 10,139,464 B2 | 11/2018 | Rearick et al. |
| 10,145,913 B2 | 12/2018 | Hugon et al. |
| 10,145,922 B2 | 12/2018 | Rothberg et al. |
| 10,162,026 B2 | 12/2018 | Walsh |
| 10,222,434 B2 | 3/2019 | Poole et al. |
| 10,222,435 B2 | 3/2019 | Mileski et al. |
| 10,241,177 B2 | 3/2019 | Poole et al. |
| 10,274,561 B2 | 4/2019 | Poole et al. |
| 10,281,540 B2 | 5/2019 | Mileski et al. |
| 10,281,541 B2 | 5/2019 | Poole et al. |
| 10,295,628 B2 | 5/2019 | Mileski et al. |
| 10,310,037 B2 | 6/2019 | McNulty et al. |
| 10,317,502 B2 | 6/2019 | Harvey et al. |
| 10,324,147 B2 | 6/2019 | McNulty et al. |
| 10,330,755 B2 | 6/2019 | Poole et al. |
| 10,353,030 B2 | 7/2019 | Poole et al. |
| 10,371,773 B2 | 8/2019 | Poole et al. |
| 10,379,186 B2 | 8/2019 | Rothberg et al. |
| 10,416,264 B2 | 9/2019 | Sofka et al. |
| 10,444,310 B2 | 10/2019 | Poole et al. |
| 10,466,327 B2 | 11/2019 | Rothberg et al. |
| 10,488,482 B2 | 11/2019 | Rearick et al. |
| 10,495,712 B2 | 12/2019 | Rothberg et al. |
| 10,520,566 B2 | 12/2019 | Poole et al. |
| 10,527,692 B2 | 1/2020 | McNulty et al. |
| 10,534,058 B2 | 1/2020 | Sofka et al. |
| 10,539,637 B2 | 1/2020 | Poole et al. |
| 10,545,207 B2 | 1/2020 | Poole et al. |
| 10,551,452 B2 | 2/2020 | Rearick et al. |
| 10,564,239 B2 | 2/2020 | Poole et al. |
| 10,591,561 B2 | 3/2020 | Sacolick et al. |
| 10,709,387 B2 | 7/2020 | Poole et al. |
| 10,866,293 B2 | 12/2020 | O'Halloran et al. |
| 11,221,386 B2 | 1/2022 | Rearick et al. |
| 2002/0084782 A1 | 7/2002 | Guthrie |
| 2002/0097049 A1 | 7/2002 | Goto |
| 2002/0149365 A1 | 10/2002 | DeMeester et al. |
| 2003/0160616 A1 | 8/2003 | Asano et al. |
| 2004/0021464 A1 | 2/2004 | Fahrig et al. |
| 2004/0039277 A1 | 2/2004 | Watanbe et al. |
| 2004/0164736 A1 | 8/2004 | Guthausen et al. |
| 2004/0164739 A1 | 8/2004 | Peterson et al. |
| 2004/0204644 A1 | 10/2004 | Tsougarakis et al. |
| 2005/0168221 A1 | 8/2005 | Miyoshi |
| 2005/0171422 A1 | 8/2005 | Zhang |
| 2005/0270023 A1 | 12/2005 | Freedman |
| 2006/0022674 A1 | 2/2006 | Zhou et al. |
| 2006/0089544 A1 | 4/2006 | Williams, Jr. et al. |
| 2006/0164082 A1 | 7/2006 | Foxall et al. |
| 2006/0255807 A1 | 11/2006 | McBride |
| 2007/0078334 A1 | 4/2007 | Scully et al. |
| 2007/0182410 A1 | 8/2007 | Niemi et al. |
| 2007/0258543 A1 | 11/2007 | Huber |
| 2008/0048658 A1 | 2/2008 | Hushek et al. |
| 2008/0111547 A1 | 5/2008 | Alsop |
| 2008/0315879 A1 | 12/2008 | Saha |
| 2009/0257634 A1 | 10/2009 | Moeller et al. |
| 2010/0019766 A1 | 1/2010 | Zuehlsdorff et al. |
| 2010/0033185 A1 | 2/2010 | Saha et al. |
| 2010/0045291 A1 | 2/2010 | Greiser et al. |
| 2010/0141257 A1 | 6/2010 | Graesslin et al. |
| 2010/0142785 A1 | 6/2010 | Dahnke et al. |
| 2010/0213938 A1 | 8/2010 | Jeong et al. |
| 2010/0219828 A1 | 9/2010 | Takahashi et al. |
| 2010/0237861 A1 | 9/2010 | Hennel |
| 2010/0244825 A1 | 9/2010 | Brau et al. |
| 2010/0331667 A1 | 12/2010 | Nelson |
| 2011/0190619 A1 | 8/2011 | Good |
| 2011/0257512 A1 | 10/2011 | Krueger |
| 2011/0299456 A1 | 12/2011 | Schmidt et al. |
| 2012/0010497 A1 | 1/2012 | Ehman et al. |
| 2012/0081120 A1 | 4/2012 | Elgort et al. |
| 2012/0086453 A1 | 4/2012 | Albu et al. |
| 2012/0092009 A1 | 4/2012 | Zhang et al. |
| 2012/0119739 A1 | 5/2012 | Gleich |
| 2012/0223709 A1 | 9/2012 | Schillak et al. |
| 2013/0082705 A1 | 4/2013 | Landschuetz et al. |
| 2013/0116544 A1 | 5/2013 | Rey et al. |
| 2013/0214783 A1 | 8/2013 | Zhao |
| 2013/0234706 A1 | 9/2013 | Mandal et al. |
| 2013/0251227 A1 | 9/2013 | Wang et al. |
| 2013/0307538 A1 | 11/2013 | Pfeuffer et al. |
| 2014/0084929 A1 | 3/2014 | Choi et al. |
| 2014/0155732 A1 | 6/2014 | Patz et al. |
| 2014/0164739 A1 | 6/2014 | Gschwind et al. |
| 2014/0203804 A1 | 7/2014 | Duensing |
| 2014/0210471 A1 | 7/2014 | Stemmer |
| 2014/0218031 A1 | 8/2014 | Lee et al. |
| 2014/0225612 A1 | 8/2014 | Polimeni et al. |
| 2014/0232393 A1 | 8/2014 | Wheaton et al. |
| 2014/0232400 A1 | 8/2014 | Kim et al. |
| 2014/0266195 A1 | 9/2014 | Levin |
| 2014/0343397 A1 | 11/2014 | Kim et al. |
| 2015/0115960 A1 | 4/2015 | Grodzki |
| 2016/0069968 A1 | 3/2016 | Rothberg et al. |
| 2016/0069970 A1 | 3/2016 | Rearick et al. |
| 2016/0069971 A1 | 3/2016 | McNulty et al. |
| 2016/0069972 A1 | 3/2016 | Poole et al. |
| 2016/0069975 A1 | 3/2016 | Rothberg et al. |
| 2016/0128592 A1 | 5/2016 | Rosen et al. |
| 2016/0131727 A1 | 5/2016 | Sacolick et al. |
| 2016/0169992 A1 | 6/2016 | Rothberg et al. |
| 2016/0169993 A1 | 6/2016 | Rearick et al. |
| 2016/0192859 A1 | 7/2016 | Shirai et al. |
| 2016/0223631 A1 | 8/2016 | Poole et al. |
| 2016/0231399 A1 | 8/2016 | Rothberg et al. |
| 2016/0231402 A1 | 8/2016 | Rothberg et al. |
| 2016/0231403 A1 | 8/2016 | Rothberg et al. |
| 2016/0231404 A1 | 8/2016 | Rothberg et al. |
| 2016/0299203 A1 | 10/2016 | Mileski et al. |

(56) References Cited

U.S. PATENT DOCUMENTS

| | | |
|---|---|---|
| 2016/0334479 A1 | 11/2016 | Poole et al. |
| 2017/0003363 A1 | 1/2017 | Rosen et al. |
| 2017/0010339 A1 | 1/2017 | Rosen et al. |
| 2017/0102443 A1 | 4/2017 | Rearick et al. |
| 2017/0108569 A1 | 4/2017 | Harvey et al. |
| 2017/0227616 A1 | 8/2017 | Poole et al. |
| 2017/0276747 A1 | 9/2017 | Hugon et al. |
| 2017/0276749 A1 | 9/2017 | Hugon et al. |
| 2017/0276751 A1 | 9/2017 | Xie et al. |
| 2018/0024208 A1 | 1/2018 | Rothberg et al. |
| 2018/0038931 A1* | 2/2018 | Rearick .................. G01R 33/28 |
| 2018/0088193 A1 | 3/2018 | Rearick et al. |
| 2018/0143274 A1 | 5/2018 | Poole et al. |
| 2018/0143275 A1 | 5/2018 | Sofka et al. |
| 2018/0143280 A1 | 5/2018 | Dyvorne et al. |
| 2018/0143281 A1 | 5/2018 | Sofka et al. |
| 2018/0144467 A1 | 5/2018 | Sofka et al. |
| 2018/0156881 A1 | 6/2018 | Poole et al. |
| 2018/0164390 A1 | 6/2018 | Poole et al. |
| 2018/0168527 A1 | 6/2018 | Poole et al. |
| 2018/0210047 A1 | 7/2018 | Poole et al. |
| 2018/0224512 A1 | 8/2018 | Poole et al. |
| 2018/0238978 A1 | 8/2018 | McNulty et al. |
| 2018/0238980 A1 | 8/2018 | Poole et al. |
| 2018/0238981 A1 | 8/2018 | Poole et al. |
| 2019/0004130 A1 | 1/2019 | Poole et al. |
| 2019/0011510 A1 | 1/2019 | Hugon et al. |
| 2019/0011513 A1 | 1/2019 | Poole et al. |
| 2019/0011514 A1 | 1/2019 | Poole et al. |
| 2019/0011521 A1 | 1/2019 | Sofka et al. |
| 2019/0018094 A1 | 1/2019 | Mileski et al. |
| 2019/0018095 A1 | 1/2019 | Mileski et al. |
| 2019/0018096 A1 | 1/2019 | Poole et al. |
| 2019/0025389 A1 | 1/2019 | McNulty et al. |
| 2019/0033402 A1 | 1/2019 | McNulty et al. |
| 2019/0033414 A1 | 1/2019 | Sofka et al. |
| 2019/0033415 A1 | 1/2019 | Sofka et al. |
| 2019/0033416 A1 | 1/2019 | Rothberg et al. |
| 2019/0038233 A1 | 2/2019 | Poole et al. |
| 2019/0086497 A1 | 3/2019 | Rearick et al. |
| 2019/0101607 A1 | 4/2019 | Rothberg et al. |
| 2019/0162806 A1 | 5/2019 | Poole et al. |
| 2019/0178962 A1 | 6/2019 | Poole et al. |
| 2019/0178963 A1 | 6/2019 | Poole et al. |
| 2019/0227136 A1 | 7/2019 | Mileski et al. |
| 2019/0227137 A1 | 7/2019 | Mileski et al. |
| 2019/0250227 A1 | 8/2019 | McNulty et al. |
| 2019/0250228 A1 | 8/2019 | McNulty et al. |
| 2019/0257903 A1 | 8/2019 | Poole et al. |
| 2019/0324098 A1 | 10/2019 | McNulty et al. |
| 2019/0353720 A1 | 11/2019 | Dyvorne et al. |
| 2019/0353723 A1 | 11/2019 | Dyvorne et al. |
| 2019/0353726 A1 | 11/2019 | Poole et al. |
| 2019/0353727 A1 | 11/2019 | Dyvorne et al. |
| 2020/0011952 A1 | 1/2020 | Rothberg et al. |
| 2020/0018806 A1 | 1/2020 | Rothberg et al. |
| 2020/0022611 A1 | 1/2020 | Nelson et al. |
| 2020/0022612 A1 | 1/2020 | McNulty et al. |
| 2020/0022613 A1 | 1/2020 | Nelson et al. |
| 2020/0025846 A1 | 1/2020 | Nelson et al. |
| 2020/0025851 A1 | 1/2020 | Rearick et al. |
| 2020/0033431 A1 | 1/2020 | Schlemper et al. |
| 2020/0034998 A1 | 1/2020 | Schlemper et al. |
| 2020/0041588 A1 | 2/2020 | O'Halloran et al. |
| 2020/0045112 A1 | 2/2020 | Sacolick et al. |
| 2020/0058106 A1 | 2/2020 | Lazarus et al. |
| 2020/0150202 A1 | 5/2020 | Hugon et al. |
| 2020/0200844 A1 | 6/2020 | Boskamp et al. |
| 2020/0209334 A1 | 7/2020 | O'Halloran et al. |
| 2020/0249297 A1 | 8/2020 | Sacolick et al. |
| 2020/0289019 A1 | 9/2020 | Schlemper et al. |
| 2020/0289022 A1 | 9/2020 | Coumans et al. |
| 2020/0294229 A1 | 9/2020 | Schlemper et al. |
| 2020/0294282 A1 | 9/2020 | Schlemper et al. |
| 2020/0294287 A1 | 9/2020 | Schlemper et al. |
| 2020/0355765 A1 | 11/2020 | Chen et al. |

FOREIGN PATENT DOCUMENTS

| | | |
|---|---|---|
| EP | 1262786 A2 | 12/2002 |
| JP | S60-063972 A | 4/1985 |
| JP | H01-242057 A | 9/1989 |
| JP | H03-188831 A | 8/1991 |
| JP | H05-344960 A | 12/1993 |
| JP | 2001-517510 A | 10/2001 |
| JP | 2004-255189 A | 9/2004 |
| JP | 2005-509507 A | 4/2005 |
| JP | 2005-524453 A | 8/2005 |
| JP | 2006-280930 A | 10/2006 |
| JP | 2012-029999 A | 2/2012 |
| JP | 2014-121384 A | 7/2014 |
| JP | 2014-523795 A | 9/2014 |
| WO | WO 2010/029725 A1 | 3/2010 |
| WO | WO 2013/016639 A1 | 1/2013 |
| WO | WO 2014/076808 A1 | 5/2014 |
| WO | WO 2015/150236 A1 | 10/2015 |

OTHER PUBLICATIONS

U.S. Appl. No. 16/806,532, filed Mar. 2, 2020, Sacolick et al.
U.S. Appl. No. 16/527,327, filed Jul. 31, 2019, O'Halloran et al.
U.S. Appl. No. 17/086,869, filed Nov. 2, 2020, O'Halloran et al.
EP 15858711.3, Jun. 18, 2018, Extended European Search Report.
PCT/US2015/060117, Feb. 25, 2016, International Search Report and Written Opinion.
PCT/US2015/060177, Jan. 7, 2016, Invitation to Pay Additional Fees.
PCT/US2019/044262, Nov. 11, 2019, International Search Report and Written Opinion.
PCT/US2020/061281, Mar. 4, 2021, International Search Report and Written Opinion.
U.S. Appl. No. 16/583,190, filed Sep. 25, 2019, Rearick et al.
EP 15838773.8, Apr. 6, 2018, Extended European Search Report.
PCT/US2015/048479, Dec. 8, 2015, International Search Report and Written Opinion.
International Search Report and Written Opinion for International Application No. PCT/US2020/061281 dated Mar. 4, 2021.
Jwo et al., Windowing Design and Performance Assessment for Mitigation of Spectrum Leakage. E3S Web of Conferences, EDP Sciences. Jan. 1, 2019;94:1-8.
Extended European Search Report for European Application No. 15858711.3 dated Jun. 18, 2018.
International Search Report and Written Opinion for International Application No. PCT/US2019/044262 dated Nov. 11, 2019.
International Search Report and Written Opinion for International Application No. PCT/US2015/060117 dated Feb. 25, 2016.
Invitation to Pay Additional Fees for International Application No. PCT/US2015/060177 dated Jan. 7, 2016.
Blanco et al., Interventional and intraoperative MRI at low field scanner—a review. European Journal of Radiology, Elsevier Science. 2005;56(2): 130-42.
Block et al., Undersampled Radial MRI with Multiple Coils. Iterative Image Reconstruction Using a Total Variation Constraint. Magnetic Resonance in Medicine. 2007;57:1086-98.
Buonocore et al., Ghost artifact reduction for echo planar imaging using image phase correction. Magnetic resonance in medicine. Jul. 1997;38(1):89-100.
Gao et al., Distortion-free diffusion MRI using an MRI-guided Tri-Cobalt 60 radiotherapy system: sequence verification and preliminary clinical experience. Medical physics. Oct. 2017;44(10):5357-66.
Grodzki et al., Quiet T1-weighted head scanning using PETRA. Proc. Intl. Soc. Mag. Reson. Med. 2013;21:0456.
Grodzki, Entwicklung von neuen Sequenzen mit ultrakurzen Echozeiten für die klinische Magnetresonanzbildgebung. 2011. 109 pages.

(56) References Cited

OTHER PUBLICATIONS

Haacke et al., Susceptibility-Weighted Imaging: Technical Aspects and Clinical Applications, Part 1. AJNR Am J Neuroradiol. 2009;30:19-30.
Jackson et al., Selection of a Convolution Function for Fourier Inversion Using Gridding. IEEE Transactions on Medical Imaging. 1991;10(3):473-8.
Li et al., Correction of Excitation Profile in Zero Echo Time (ZTE) Imaging Using Quadratic Phase-Modulated RF Pulse Excitation and Iterative Reconstruction. IEEE Trans Med Imaging. Apr. 2014; 33(4):961-9. retrieved on Feb. 10, 2016: http://www.ncbi.nlm.nih.gov/pmc/articles/PMC4136480.
Weiger et al., MRI with Zero Echo Time: Hard Versus Sweep Pulse Excitation. Magnetic Resonance in Medicine. 2011;66:379-89.
Wu et al., Water- and Fat-Suppressed Proton Projection MRI (WASPI) of Rat Femur Bone. Magnetic Resonance in Medicine 2007;57:554-67.
International Preliminary Report on Patentability for International Application No. PCT/US2020/061281 dated Jun. 9, 2022.
Communication pursuant to Article 94(3) EPC dated Aug. 19, 2021 in connection with European Application No. 15838773.8.
U.S. Appl. No. 17/541,070, filed Dec. 2, 2021, Rearick et al.
Extended European Search Report for European Application No. 15838773.8 dated Apr. 6, 2018.
International Search Report and Written Opinion for International Application No. PCT/US2015/048479 dated Dec. 8, 2015.
Blumich et al., NMR at low magnetic fields. Chemical Physics Letters. Aug. 6, 2009;477(4-6):231-40.
Danieli et al., Mobile sensor for high resolution NMR spectroscopy and imaging. Journal of Magnetic Resonance. May 1, 2009;198(1):80-7.
Issadore et al., Miniature magnetic resonance system for point-of-care diagnostics. Lab on a Chip. 2011;11(13):2282-7.
EP 15838773.8, Aug. 19, 2021, Communication pursuant to Article 94(3) EPC.

\* cited by examiner

TECHNIQUES FOR NOISE SUPPRESSION IN AN ENVIRONMENT OF A MAGNETIC RESONANCE IMAGING SYSTEM

CROSS-REFERENCE TO RELATED APPLICATIONS

This application claims the benefit under 35 U.S.C. § 119(e) of U.S. provisional patent application Ser. No. 62/941,369, entitled "TECHNIQUES FOR NOISE SUPPRESSION IN AN ENVIRONMENT OF A MAGNETIC RESONANCE IMAGING SYSTEM" filed Nov. 27, 2019, and of U.S. provisional patent application Ser. No. 62/941,940, entitled "TECHNIQUES FOR NOISE SUPPRESSION IN AN ENVIRONMENT OF A MAGNETIC RESONANCE IMAGING SYSTEM" filed Nov. 29, 2019 under each of which are incorporated by reference in their entireties herein.

BACKGROUND

Magnetic resonance imaging (MRI) provides an important imaging modality for numerous applications and is widely utilized in clinical and research settings to produce images of the inside of the human body. As a generality, MRI is based on detecting magnetic resonance (MR) signals, which are electromagnetic waves emitted by atoms in response to state changes resulting from applied electromagnetic fields. For example, nuclear magnetic resonance (NMR) techniques involve detecting MR signals emitted from the nuclei of excited atoms upon the re-alignment or relaxation of the nuclear spin of atoms in an object being imaged (e.g., atoms in the tissue of the human body). Detected MR signals may be processed to produce images, which in the context of medical applications, allows for the investigation of internal structures and/or biological processes within the body for diagnostic, therapeutic and/or research purposes.

MRI provides an attractive imaging modality for biological imaging due to the ability to produce non-invasive images having relatively high resolution and contrast without the safety concerns of other modalities (e.g., without needing to expose the subject to ionizing radiation, e.g., x-rays, or introducing radioactive material to the body). Additionally, MRI is particularly well suited to provide soft tissue contrast, which can be exploited to image subject matter that other imaging modalities are incapable of satisfactorily imaging. Moreover, MR techniques are capable of capturing information about structures and/or biological processes that other modalities are incapable of acquiring. However, there are a number of drawbacks to MRI that, for a given imaging application, may involve the relatively high cost of the equipment, limited availability (e.g., difficulty in gaining access to clinical MRI scanners) and/or the length of the image acquisition process.

The trend in clinical MRI has been to increase the field strength of MRI scanners to improve one or more of scan time, image resolution, and image contrast, which, in turn, continues to drive up costs. The vast majority of installed MRI scanners operate at 1.5 or 3 tesla (T), which refers to the field strength of the main magnetic field $B_0$. A rough cost estimate for a clinical MRI scanner is approximately one million dollars per tesla, which does not factor in the substantial operation, service, and maintenance costs involved in operating such MRI scanners.

These high-field MRI systems typically require large superconducting magnets and associated electronics to generate a strong uniform static magnetic field ($B_0$) in which an object (e.g., a patient) is imaged. The size of such systems is considerable with a typical high-field MRI installment including multiple rooms for the magnet, electronics, thermal management system, and control console areas. The size and expense of high-field MRI systems generally limits their usage to facilities, such as hospitals and academic research centers, which have sufficient space and resources to purchase and maintain them. The high cost and substantial space requirements of high-field MRI systems results in limited availability of MRI scanners. As such, there are frequently clinical situations in which an MRI scan would be beneficial, but due to one or more of the limitations discussed above, is not practical or is impossible, as discussed in further detail below.

SUMMARY

The inventors have developed noise suppression and/or avoidance techniques that are based on noise measurements obtained from the environment. The noise measurements are subsequently used to reduce the noise present in MR signals detected by a magnetic resonance imaging (MRI) system during operation, either by suppressing the environmental noise, configuring the MRI system to operate in a frequency band or bin having less noise, or both.

Some embodiments provide for a method of suppressing noise in an environment of a magnetic resonance imaging system, the method comprising: obtaining, using at least one primary coil and at least one auxiliary sensor different from the at least one primary coil, multiple calibration signals comprising a first plurality of calibration signals and a corresponding second plurality of calibration signals by: obtaining the first plurality of calibration signals using the at least one auxiliary sensor, wherein each of the first plurality of calibration signals comprises multiple values; and obtaining the second plurality of calibration signals using the at least one primary coil, wherein each of the second plurality of calibration signals comprises multiple values; weighting the multiple calibration signals to obtain multiple weighted calibration signals at least in part by: weighting at least some of the first plurality of calibration signals using a weighting function (e.g., a step weighting function in k-space, a linear weighting function in k-space, a Gaussian weighting function in k-space); and weighting at least some of the second plurality of calibration signals using the weighting function; estimating, using the multiple weighted calibration signals, a transform that, when applied to noise received by the at least one auxiliary sensor, provides an estimate of noise received by the at least one primary coil; and after estimating the transform: receiving a magnetic resonance signal using the at least one primary coil; receiving a noise signal using the at least one auxiliary sensor; estimating noise present in the magnetic resonance signal received by the at least one primary coil by applying the transform to the noise signal received by the at least one auxiliary sensor to obtain a noise estimate; and suppressing noise in the magnetic resonance signal using the noise estimate.

A magnetic resonance imaging (MRI) system comprising: at least one primary coil; at least one auxiliary sensor different from the at least one primary coil; and at least one controller configured to: cause the at least one auxiliary sensor and the at least one primary coil to obtain a first plurality of calibration signals and a second plurality of calibration signals, respectively, from an environment of the magnetic resonance imaging system, wherein each of the first plurality of calibration signals includes multiple values and each of the second plurality of calibration signals includes multiple values; weight at least some of the first plurality of calibration signals using a weighting function; weight at least some of the second plurality of calibration signals using the weighting function; estimate, based on the first plurality of calibration signals and the second plurality of calibration signals, a transform that, when applied to noise received by the at least one auxiliary sensor, provides an estimate of noise received by the at least one primary coil; and after estimating the transform: cause the at least one primary coil to receive a magnetic resonance signal; cause the at least one auxiliary sensor to receive a noise signal; estimate noise present in the magnetic resonance signal received by the at least one primary coil by applying the transform to the noise signal received by the at least one auxiliary sensor to obtain a noise estimate; and suppress noise in the magnetic resonance signal using the noise estimate.

BRIEF DESCRIPTION OF THE DRAWINGS

Various aspects and embodiments of the disclosed technology will be described with reference to the following figures. It should be appreciated that the figures are not necessarily drawn to scale.

DETAILED DESCRIPTION

Figure 1:
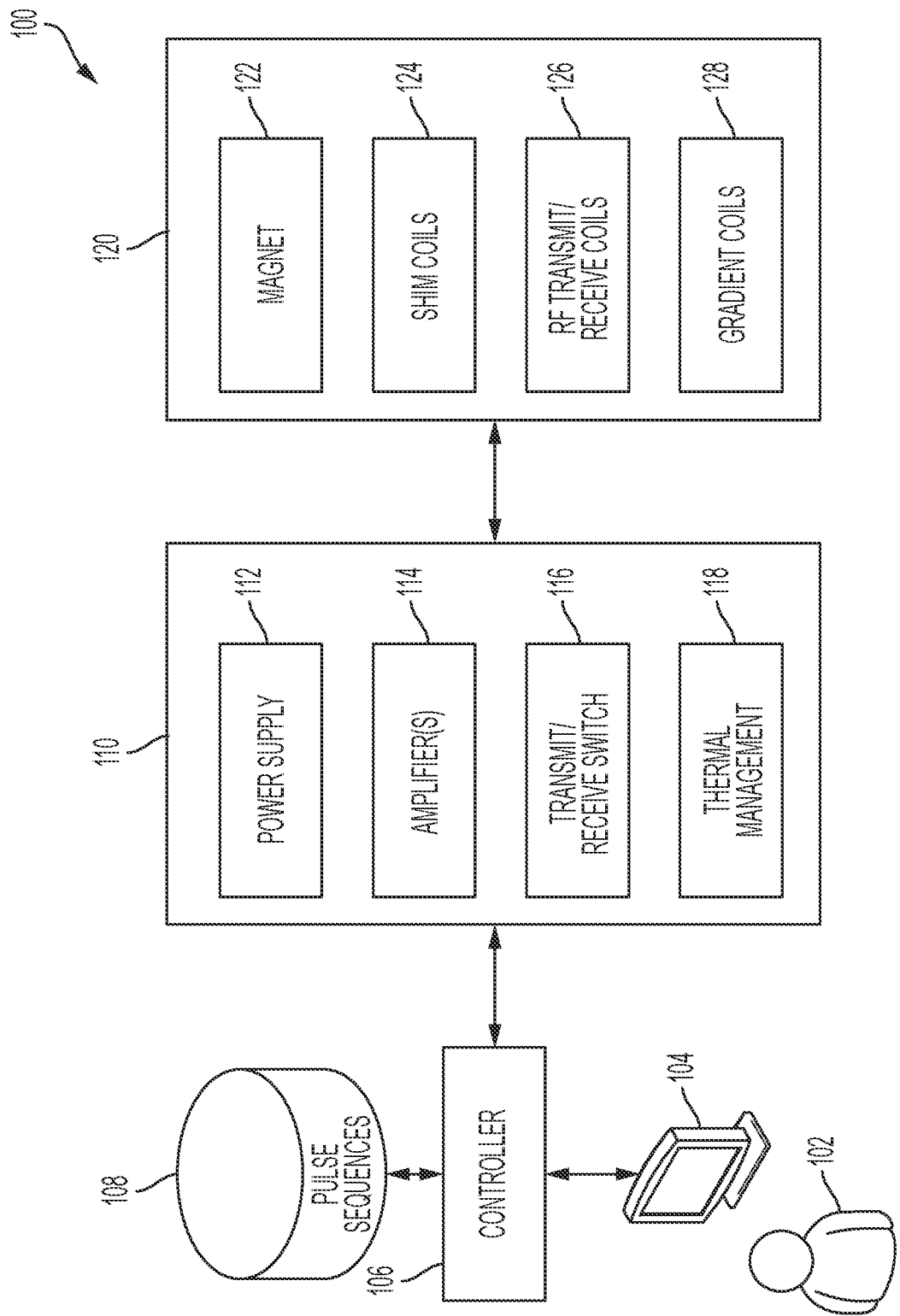
FIG. 1 illustrates a block diagram of illustrative components of a magnetic resonance imaging (MRI) system.

The MRI scanner market is overwhelmingly dominated by high-field systems, and is exclusively so for medical or clinical MRI applications. As discussed above, the general trend in medical imaging has been to produce MRI scanners with increasingly greater field strengths, with the vast majority of clinical MRI scanners operating at 1.5 T or 3 T, with higher field strengths of 7 T and 9 T used in research settings. As used herein, "high-field" refers generally to MRI systems presently in use in a clinical setting and, more particularly, to MRI systems operating with a main magnetic field (i.e., a BO field) at or above 1.5 T, though clinical systems operating between 0.5 T and 1.5 T are typically also considered "high-field." By contrast, "low-field" refers generally to MRI systems operating with a BO field of less than or equal to approximately 0.2 T.

The appeal of high-field MRI systems include improved resolution and/or reduced scan times compared to lower field systems, motivating the push for higher and higher field strengths for clinical and medical MRI applications. However, as discussed above, increasing the field strength of MRI systems yields increasingly more expensive and complex MRI scanners, thus limiting availability and preventing their use as a general purpose and/or generally available imaging solution.

Low-field MRI has been explored in limited contexts for non-imaging research purposes and narrow and specific contrast-enhanced imaging applications, but is conventionally regarded as being unsuitable for producing clinically useful images. For example, the resolution, contrast, and/or image acquisition time is generally not regarded as being suitable for clinical purposes such as, but not limited to, tissue differentiation, blood flow or perfusion imaging, diffusion-weighted (DW) or diffusion tensor (DT) imaging, functional MRI (fMRI), etc.

The inventors have developed techniques for producing improved quality, portable and/or lower-cost low-field MRI systems that can improve the wide-scale deployability of MRI technology in a variety of environments beyond the large MRI installments at hospitals and research facilities. As such, low-field MRI presents an attractive imaging solution, providing a relatively low cost, high availability alternative to high-field MRI. In particular, low-field MRI systems can be implemented as self-contained systems that are deployable in a wide variety of clinical settings where high-field MRI systems cannot, for example, by virtue of being transportable, cartable or otherwise generally mobile so as to be deployable where needed. As a result, such low-field MRI systems may be expected to operate in generally unshielded or partially shielded environments (e.g., outside of specially shielded rooms or encompassing cages) and handle the particular noise environment in which they are deployed.

Some aspects of the inventors' contribution derive from their recognition that performance of a flexible low-field MRI systems (e.g., a generally mobile, transportable or cartable system and/or a system that can be installed in a variety of settings such as in an emergency room, office or clinic) may be particularly vulnerable to noise, such as RF interference, to which many conventional high field MRI systems are largely immune due to being installed in specialized rooms with extensive shielding. In particular, such systems may be required to operate in unshielded or partially shielded environments, as well as in multiple environments that may have different and/or variable sources of noise to contend with.

To facilitate low field MRI systems that can be flexibly and widely deployed, the inventors have developed noise suppression techniques for use with low-field MRI systems in order to eliminate or mitigate unwanted noise or to reduce its impact on the operation of the low-field systems. According to some embodiments, noise suppression and/or avoidance techniques are based on noise measurements obtained from the environment. The noise measurements are subsequently used to reduce the noise present in MR signals detected by the low-field MRI system (e.g., a system having a $B_0$ field of approximately 0.2 T or less, approximately 0.1

T or less, approximately 50 mT or less, approximately 20 mT or less, approximately 10 mT or less, between 50 mT and 0.1 T, between 0.1 T and 0.2 T, etc.) during operation, either by suppressing the environmental noise, configuring the low-field MRI system to operate in a frequency band or bin having less noise, or both. Thus, the low-field MRI system compensates for noise present in whatever environment the system is deployed and can therefore operate in unshielded or partially shielded environments and are not limited to specialized shielded rooms.

Noise suppression techniques developed by the inventors are described in more detail below and it should be appreciated that the noise suppression techniques described herein may be used with any suitable low-field or high-field MRI systems deployed in virtually any facility, including portable and cartable MRI systems. Non-limiting examples of low-field MRI systems for which the noise suppression techniques described herein may be used are described in U.S. Pat. No. 10,222,434, dated Mar. 5, 2019, titled "Portable Magnetic Resonance Imaging Methods and Apparatus," which is herein incorporated by reference in its entirety. While aspects of noise suppression described herein may be particularly beneficial in the low-field context where extensive shielding may be unavailable or otherwise not provided, it should be appreciated that the techniques described herein are also suitable in the high-field context and are not limited for use with any particular type of MRI system.

Accordingly, aspects of the technology described herein relate to improving the performance of low-field MRI systems in environments where the presence of noise, such as RF interference, may adversely impact the performance of such systems. In some embodiments, a low-field MRI system may be configured to detect noise (e.g., environmental noise, internal system noise, radio frequency interference, etc.) and, in response, adapt the low-field MRI system to reduce the impact of the noise on the operation of the system. The low-field MRI system may be configured to reduce the impact of the noise by suppressing noise in the RF signal obtained by the RF receive coil, by generating RF signals that destructively interfere with noise in the environment (e.g., RF interference), by adjusting characteristics of the magnetic fields produced (e.g., adjusting the magnetic field strength of the BO magnet) and/or received by the low-field MRI system so that the transmit/receive coils operate in a frequency band satisfactorily free from interference, or using a combination of these techniques.

According to some embodiments, noise suppression techniques described herein allow a MRI system to be operated in unshielded or partially shielded environments, at least in part by adapting noise compensation to the particular environment in which the MRI system is deployed. As a result, deployment of an MRI system is not confined to specially shielded rooms or other customized facilities and instead can be operated in a wide variety of environments.

In some embodiments, a system may be configured to obtain information about noise in the system's environment or within the system itself (e.g., RF interference) and suppress noise in the RF signal measured by the RF receive coil based, at least in part, on the obtained information. The system may be configured to obtain information about noise in the environment by using one or more auxiliary sensors. The term "auxiliary" is used to differentiate between a sensor or detector capable of detecting noise and the primary receive channel that receives MR signals for use in MRI. It should be appreciated that, in some embodiments, an auxiliary sensor may also receive one or more MR signals. For example, the low-field MRI system may comprise one or more auxiliary RF receive coils positioned proximate to the primary transmit/receive coil(s), but outside of the field of view of the BO field, to detect RF noise without detecting MR signals emitted by a subject being imaged. The noise detected by the auxiliary RF coil(s) may be used to suppress the noise in the MR signal obtained by the primary RF coil of the MRI system.

Such an arrangement has the ability to dynamically detect and suppress RF noise to facilitate the provision of, for example, a generally transportable and/or cartable low-field MRI system that is likely to be subjected to different and/or varying levels of RF noise depending on the environment in which the low-field MRI system is operated. That is, because noise suppression is based on the current noise environment, techniques described herein provide noise suppression capability specific to the particular environment in which the system is deployed.

The inventors have recognized that the simplistic approach of subtracting samples of noise obtained by one or more auxiliary sensors from the signal measured by the primary receive coil(s) may provide unsatisfactory noise suppression, even if the gain of the noise detected by the auxiliary sensor(s) is adjusted. The primary receive coil(s) and the auxiliary sensor(s) may measure different noise signals because the primary coil(s) and the auxiliary sensor(s) may be in different locations, have different orientations, and/or may have different physical characteristics (e.g., may have a different number of coil turns, may differ in size, shape, impedance, or may be a different type of sensor altogether).

Different locations and/or orientations of the primary coil(s) and the auxiliary sensor(s) may lead to differences in the characteristics of the noise signals received by the primary coil and the auxiliary sensor. Different physical characteristics between the primary coil(s) and auxiliary sensor(s) may lead to frequency-dependent differences between noise signals received by the primary coil(s) and auxiliary sensor(s). As a result, subtracting the noise signal measured by one or more auxiliary sensors from the signal measured by the primary coil(s) may not adequately suppress noise detected by the primary coil(s). Even if the noise signal measured by the auxiliary sensor(s) were scaled by a constant in an attempt to compensate for differences in the gain of the noise signals received by the primary coil(s) and auxiliary sensor(s), such compensation would not account for frequency-dependent differences in the noise signals.

Accordingly, in some embodiments, a transform (e.g., a transfer function, impulse response, etc.) is estimated and used to suppress noise in the RF signal received by one or more primary receive coil(s) of a low-field MRI system. As discussed in further detail below, the transform may operate to transform a noise signal received via one or multiple auxiliary sensors (e.g., one or more auxiliary RF coils and/or other types of sensors described herein) to an estimate of the noise received by the primary receive coil (or multiple primary receive coils). In some embodiments, noise suppression may comprise: (1) obtaining samples of noise by using the one or more auxiliary sensor(s); (2) obtaining samples of the MR data using the primary RF coil; (3) obtaining a transform; (4) transforming the noise samples using the transform; and (5) subtracting the transformed noise samples from the obtained MR data to suppress and/or eliminate noise.

The transform may be estimated from multiple (e.g., at least ten, at least 100, at least 1000, etc.) calibration measurements obtained using the auxiliary sensor(s) and primary coil(s). Multiple calibration measurements allow for estimating the transform with high accuracy and, in particular, may allow for estimating the amplitude and phase of the transform for a plurality of frequency bins across the frequency spectrum for which the transform is defined. For example, when processing signals using an K-point DFT (e.g., where K is an integer equal to 128, 256, 512, 1024 etc.), multiple measurements may allow for estimating the amplitude and phase of the transform for each of the K frequency bins.

In some embodiments, each calibration measurement of the multiple calibration measurements obtained by the respective sensors comprises multiple values. For example, in some embodiments, each calibration measurement obtained by the auxiliary sensor is a time series of values measured at a respective series of times using the auxiliary sensor. In some embodiments, each calibration measurement obtained by the primary coil is a time series of values measured at a respective series of times using the primary coil.

In some embodiments, the calibration measurements are weighted prior to being used for estimating the transform. For example, the calibration measurements may be weighted to de-emphasize portions of the calibration signals during which it is expected that more MR signal than noise will be detected when imaging a patient. This generally correlates to the K-space location of the sample (e.g., the signal to noise ratio is expected to be higher when acquiring signals at or near center of k-space). Such signal portions can impact the performance of the denoising algorithm. The weighting developed by the inventors can compensate for this.

In some embodiments, multiple auxiliary receive coils may be used as auxiliary sensors to suppress noise received by the primary transmit/receive coil(s) of a low-field MRI system. For example, in some embodiments, a low-field MRI system may include multiple RF coils positioned/configured to sense the MR signal emitted by the subject being imaged (e.g., multiple "primary" coils) and/or multiple coils positioned/configured to receive noise data, but to detect little or no MR signal (e.g., multiple "auxiliary" coils). Such an arrangement facilitates detection and characterization of multiple noise sources to suppress a variety of noise that may be present in a given environment. Multiple primary receive coils may also be used that factor into the noise characterization techniques described herein, as well as being used to accelerate image acquisition via parallel MR, or in other suitable ways, as discussed in further detail below. In some embodiments, eight or sixteen primary RF coils may be employed. In some embodiments, eight or sixteen auxiliary coils may be employed.

In some embodiments, multiple auxiliary sensors may be used to perform noise compensation when there are multiple sources of noise in the environment of the low-field MRI system. For example, one or more auxiliary RF coils and/or one or more other types of sensors may be used to obtain information about the noise environment resulting from noise produced by multiple sources, which information in turn may be used to process the RF signal received by the primary receive coil(s) in order to compensate for the noise produced by multiple sources. For example, in some embodiments, a multichannel transform, such as a multi-channel transfer function, may be estimated from calibration measurements obtained using multiple auxiliary sensors and the primary RF coil(s), as described in more detail below. The multichannel transform may represent the relationships among the noise signals captured by the primary RF coil(s) and each of the multiple auxiliary sensors. For example, the transform may capture correlation among the noise signals received by the multiple auxiliary sensors. The transform may also capture correlation among the noise signals receive by the multiple auxiliary sensors and the noise signal received by the primary RF coil(s).

In some embodiments, multiple auxiliary sensors may be used to perform noise suppression by: (1) obtaining samples of noise by using multiple auxiliary sensors; (2) obtaining samples of the MR data using the primary RF coil(s); (3) obtaining a multichannel transform; (4) transforming the noise samples using the multichannel transform; and (5) subtracting the transformed noise samples from the obtained MR data to suppress and/or eliminate noise.

In some embodiments, the multichannel transform may be estimated from multiple (e.g., at least ten, at least 100, at least 1000, etc.) calibration measurements. The multiple calibration measurements allow for estimating the multichannel transform with high accuracy and, in particular, may allow for estimating the amplitude and phase of the transform for a plurality of frequency bins across which the multichannel transfer function is defined. For example, when processing signals using a K-point DFT (e.g., where K is an integer equal to 128, 256, 512, 1024 etc.), multiple calibration measurements may allow for estimating the amplitude and phase of the multichannel transform for each of the K frequency bins.

The inventors have further appreciated that the MR signal detected by one or more primary receive coils may also be utilized to characterize the noise to suppress or eliminate noise from the MR data. In particular, the inventors have recognized that by repeating MR data acquisitions using the same spatial encoding (e.g., by repeating a pulse sequence with the same operating parameters for the gradient coils), the "redundant" data acquired can be used to characterize the noise. For example, if a pulse sequence is repeated with the same spatial encoding multiple times, the MR data obtained should in theory be the same. Thus, the difference in the signals acquired from multiple acquisitions using the same spatial encoding can be presumed to have resulted from noise. Accordingly, multiple signals obtained from using the same spatial encoding may be phase shifted and subtracted (or added) to obtain a measure of the noise.

According to some embodiments, noise characterized in this manner can be used to compute a transform or included as a channel in a multi-channel transform, as discussed in further detail below. Alternatively, noise characterized in this manner can be used alone or in combination with other techniques to suppress noise from acquired MR signals. For example, a noise estimate obtained based on multiple MR signals obtained using the same spatial encoding may be used to suppress noise without computing a transform, as other suitable techniques may be used.

The inventors have further appreciated that one or more sensors (e.g., one or more RF coils or other sensors capable of detecting electromagnetic fields) may be used to assess the noise background in a spectrum of interest to assess which band within the spectrum is cleanest from a noise perspective so that the transmit/receive coil(s) may be configured to operate in the identified frequency band. Accordingly, in some embodiments, a low-field MRI system may be adapted by adjusting the transmit/receive coil(s) to operate at a frequency band having less interference relative to other frequency bands in which the transmit/receive coil(s) can be configured to operate. For example, one or more auxiliary RF coils may be configured to monitor noise across multiple frequency bands over which the primary RF coil could operate and, the primary RF coil may be configured to operate at the frequency band having the least amount of noise, as determined by the measurements obtained using the auxiliary RF coils. In particular, an auxiliary RF coil may be a wideband RF coil configured to measure the noise level (e.g., noise floor) across a wide band of frequencies. Based on the noise measured across a frequency band of interest, the primary transmit/receive coil(s) (e.g., which may be a narrowband coil) may be configured to operate in a band determined to have less noise than other frequency bands. Alternatively, multiple sensors may be provided, each measuring noise levels in a respective frequency band. The primary transmit/receive coil(s) may then be configured to operate in the frequency band determined to have the least amount of noise present.

The inventors have also appreciated that a significant source of interference for a low-field MRI system may be one or more power lines (e.g., power cords) supplying power to the low-field MRI system. Accordingly, in some embodiments, a low-field MRI system is configured to measure directly any interference due to the power line(s) and use the measurements to suppress or cancel such interference. For example, in some embodiments, a low-field MRI system may include one or more sensors coupled to a power line of the system to measure any RF signals produced or carried by the power line, and the measurements obtained by the sensor(s) may be used as part of the noise suppression techniques described herein (e.g., to further characterize the noise environment and facilitate estimation of a comprehensive transfer function).

In some embodiments, a low-field MRI system may include an antenna capacitively coupled to one of the power lines of the system and may be configured to use measurements obtained by the antenna to suppress noise in the RF signal received by the primary RF coil of the low-field MRI system. Such an antenna may be of any suitable type and, for example, may comprise a thin metal sheet wrapped around the power line and/or one or more capacitors coupled to the power line. A low-field MRI system may include multiple such antenna to detect noise resulting from any desired number of power lines supplying power to the system (or that otherwise impact the system) including, for example, hot lines carrying single-phase, two-phase, or three-phase power. In some instances, a low-field MRI system may include such an antenna for a ground wire. As another example, a low-field MRI system may include a sensor inductively coupled to a power line or multiple respective power lines (e.g., by use of a toroid or any other suitable method) to measure RF signals carried by the power line such that these measurements may be used to suppress noise in the RF signal measured by the primary RF coil of the low-field MRI system.

In some embodiments, a sensor's measurements of interference due to a power line may be used to suppress noise in the RF signal measured by the primary RF receive coil by estimating a transfer function between the primary RF receive coil and the sensor. This may be done in any suitable way and, for example, may be done using the techniques described herein for estimating a transfer function between the primary RF receive coil and an auxiliary RF receive coil. For example, noise characterized in this manner may be used to estimate a transform alone or may be a channel in a multi-channel transform. Noise characterized by a sensor coupled to one or more power lines may be utilized in other manners (e.g., used directly to suppress noise), as the aspects are not limited in this respect.

The inventors have further appreciated that noise in the environment may be detected by coupling one or more sensors to one or more electromagnetic interference (EMI) shields. For example, a sensor may be connected inductively or capacitively between one or more EMI shields and ground to detect the EMI captured by the shield. Noise characterized in this manner may be used to suppress or eliminate noise from MR signals detected by the primary receive coil(s). For example, noise characterized by coupling a sensor to one or more EMI shields may be used to estimate a transform alone, or may be used as a channel in a multi-channel transform. Noise characterized by a sensor coupled to one or more EMI shields may be utilized in other manners, as the aspects are not limited in this respect.

According to some embodiments, noise from various sources are characterized using a combination of the above described techniques to determine a multi-channel transform that can be used to suppress or eliminate noise from the various noise sources. Noise measurements may be obtained during operation of the MRI system so that a multi-channel transform may be determined dynamically, allowing for noise suppression that adapts to the changing noise environment of the MRI system. However, noise in the environment may be characterized upon system start-up, when the system is moved to a different location and/or upon the occurrence of any event, and the characterized noise used to suppress and/or eliminate noise in acquired MR signals, as the techniques described herein can be applied as desired.

Following below are more detailed descriptions of various concepts related to, and embodiments of, methods and apparatus for noise suppression and/or cancellation. It should be appreciated that various aspects described herein may be implemented in any of numerous ways. Examples of specific implementations are provided herein for illustrative purposes only. In addition, the various aspects described in the embodiments below may be used alone or in any combination, and are not limited to the combinations explicitly described herein.

FIG. 1 is a block diagram of exemplary components of a MRI system 100. While the noise suppression techniques may have particular benefits for a low-field MRI system, the techniques described herein are not limited for use at low-field and may be employed to suppress noise in the high-field context, as the aspects are not limited in this respect. In the illustrative example of FIG. 1, MRI system 100 comprises workstation 104, controller 106, pulse sequences store 108, power management system 110, and magnetic components 120. It should be appreciated that system 100 is illustrative and that a MRI system may have one or more other components of any suitable type in addition to or instead of the components illustrated in FIG. 1.

As illustrated in FIG. 1, magnetic components 120 comprises $B_0$ magnet 122, shim coils 124, RF transmit and receive coils 126, and gradient coils 128. $B_0$ magnet 122 may be used to generate, at least in part, the main magnetic field $B_0$. $B_0$ magnet 122 may be any suitable type of magnet that can generate a main magnetic field (e.g., a low-field strength of approximately 0.2 T or less), and may include one or more $B_0$ coils, correction coils, etc. Shim coils 124 may be used to contribute magnetic field(s) to improve the homogeneity of the $B_0$ field generated by magnet 122. Gradient coils 128 may be arranged to provide gradient fields and, for example, may be arranged to generate gradients in the magnetic field in three substantially orthogonal directions (X, Y, Z) to localize where MR signals are induced.

In some embodiments, the $B_0$ magnet 122 may be a permanent magnet. The $B_0$ magnet 122 may be a bi-planar permanent magnet and, in some embodiments, may comprise multiple sets of concentric permanent magnet rings.

Non-limiting examples of $B_0$ magnet 122 are provided in U.S. Pat. No. 10,222,434, dated Mar. 5, 2019, titled "Portable Magnetic Resonance Imaging Methods and Apparatus," which is herein incorporated by reference in its entirety.

RF transmit and receive coils 126 may comprise one or more transmit coils that may be used to generate RF pulses to induce a magnetic field $B_1$. The transmit coil(s) may be configured to generate any suitable type of RF pulses configured to excite an MR response in a subject and detect the resulting MR signals emitted. RF transmit and receive coils 126 may include one or multiple transmit coils and one or multiple receive coils. The transmit and receive coils may be implemented using the same coils or may be implemented using separate coils for transmit and receive, and are referred to generally as transmit/receive coils or Tx/Rx coils. Each of magnetics components 120 may be constructed in any suitable way.

Power management system 110 includes electronics to provide operating power to one or more components of the low-field MRI system 100. For example, as discussed in more detail below, power management system 110 may include one or more power supplies, gradient power amplifiers, transmit coil amplifiers, and/or any other suitable power electronics needed to provide suitable operating power to energize and operate components of the low-field MRI system 100.

As illustrated in FIG. 1, power management system 110 comprises power supply 112, amplifier(s) 114, transmit/receive switch 116, and thermal management components 118. Power supply 112 includes electronics to provide operating power to magnetic components 120 of the low-field MRI system 100. For example, power supply 112 may include electronics to provide operating power to one or more $B_0$ coils (e.g., $B_0$ magnet 122) to produce the main magnetic field for the low-field MRI system. In some embodiments, power supply 112 is a unipolar, continuous wave (CW) power supply, however, any suitable power supply may be used. Transmit/receive switch 116 may be used to select whether RF transmit coils or RF receive coils are being operated.

Amplifier(s) 114 may include one or more RF receive (Rx) pre-amplifiers that amplify MR signals detected by one or more RF receive coils (e.g., coils 124), one or more RF transmit (Tx) amplifiers configured to provide power to one or more RF transmit coils (e.g., coils 126), one or more gradient power amplifiers configured to provide power to one or more gradient coils (e.g., gradient coils 128), shim amplifiers configured to provide power to one or more shim coils (e.g., shim coils 124).

Thermal management components 118 provide cooling for components of low-field MRI system 100 and may be configured to do so by facilitating the transfer of thermal energy generated by one or more components of the low-field MRI system 100 away from those components. Thermal management components 118 may include, without limitation, components to perform water-based or air-based cooling, which may be integrated with or arranged in close proximity to MRI components that generate heat including, but not limited to, $B_0$ coils, gradient coils, shim coils, and/or transmit/receive coils. Thermal management components 118 may include any suitable heat transfer medium including, but not limited to, air and water, to transfer heat away from components of the low-field MRI system 100.

As illustrated in FIG. 1, low-field MRI system 100 includes controller 106 (also referred to as a console) having control electronics to send instructions to and receive information from power management system 110. Controller 106 may be configured to implement one or more pulse sequences, which are used to determine the instructions sent to power management system 110 to operate the magnetic components 120 in a desired sequence. For example, controller 106 may be configured to control power management system 110 to operate the magnetic components 120 in accordance with a balance steady-state free precession (bSSFP) pulse sequence, a low-field gradient echo pulse sequence, a low-field spin echo pulse sequence, a low-field inversion recovery pulse sequence, and/or any other suitable pulse sequence. Controller 106 may be implemented as hardware, software, or any suitable combination of hardware and software, as aspects of the disclosure provided herein are not limited in this respect.

In some embodiments, controller 106 may be configured to implement a pulse sequence by obtaining information about the pulse sequence from pulse sequences repository 108, which stores information for each of one or more pulse sequences. Information stored by pulse sequences repository 108 for a particular pulse sequence may be any suitable information that allows controller 106 to implement the particular pulse sequence. For example, information stored in pulse sequences repository 108 for a pulse sequence may include one or more parameters for operating magnetics components 120 in accordance with the pulse sequence (e.g., parameters for operating the RF transmit and receive coils 126, parameters for operating gradient coils 128, etc.), one or more parameters for operating power management system 110 in accordance with the pulse sequence, one or more programs comprising instructions that, when executed by controller 106, cause controller 106 to control system 100 to operate in accordance with the pulse sequence, and/or any other suitable information. Information stored in pulse sequences repository 108 may be stored on one or more non-transitory storage media.

As illustrated in FIG. 1, controller 106 also interacts with computing device 104 programmed to process received MR data. For example, computing device 104 may process received MR data to generate one or more MR images using any suitable image reconstruction process(es). Controller 106 may provide information about one or more pulse sequences to computing device 104 for the processing of data by the computing device. For example, controller 106 may provide information about one or more pulse sequences to computing device 104 and the computing device may perform an image reconstruction process based, at least in part, on the provided information.

Computing device 104 may be any electronic device that may process acquired MR data and generate one or more images of the subject being imaged. In some embodiments, computing device 104 may be a fixed electronic device such as a desktop computer, a server, a rack-mounted computer, or any other suitable fixed electronic device that may be configured to process MR data and generate one or more images of the subject being imaged. Alternatively, computing device 104 may be a portable device such as a smart phone, a personal digital assistant, a laptop computer, a tablet computer, or any other portable device that may be configured to process MR data and generate one or images of the subject being imaged. In some embodiments, computing device 104 may comprise multiple computing devices of any suitable type, as the aspects are not limited in this respect. A user 102 may interact with workstation 104 to control aspects of the low-field MR system 100 (e.g., program the system 100 to operate in accordance with a particular pulse sequence, adjust one or more parameters of the system 100, etc.) and/or view images obtained by the low-field MR system 100.

Figure 2:
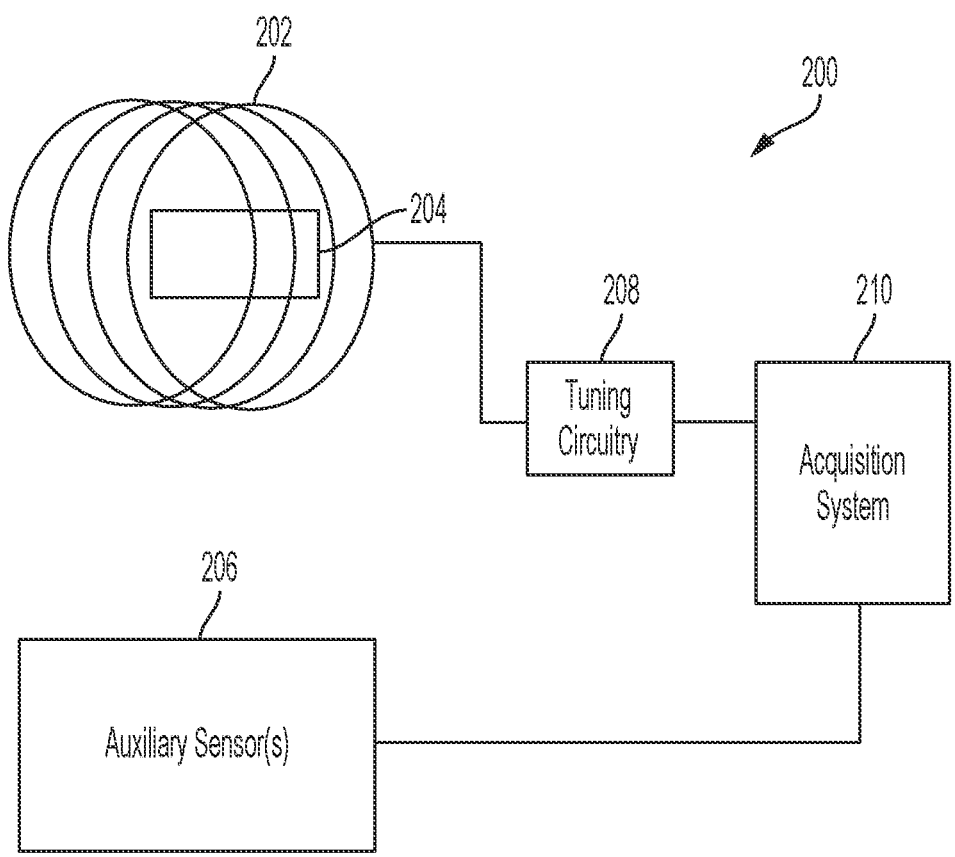
FIG. 2 illustrates exemplary components of an MRI system used for performing noise suppression, in accordance with some embodiments of the technology described herein.

FIG. 2 shows illustrative components of a portion of an example a MRI system that may be used for performing noise suppression, in accordance with some embodiments of the technology described herein. For example, transmit/receive system 200 may form at least part of the transmit/receive equipment (e.g., transmit/receive coils 126, one or more controllers, etc.) of a low-field MRI system including any of the example systems described in U.S. Pat. No. 10,222,434, dated Mar. 5, 2019, titled "Portable Magnetic Resonance Imaging Methods and Apparatus," which is herein incorporated by reference in its entirety.

Transmit/receive system 200 is configured to detect MR signals emitted from excited atoms of a subject 204 being imaged, and to characterize noise in the environment to suppress or remove the characterized noise from the detected MR signals, as discussed in further detail below.

As shown in FIG. 2, transmit/receive system 200 comprises a primary RF receive coil 202 configured to measure MR signals emitted by the subject 204 in response to an excitation pulse sequence (e.g., a pulse sequence selected from pulse sequence repository 108 and executed by controller 102). The excitation pulse sequence may be produced by primary RF receive coil 202 and/or by one or more other transmit RF coils arranged proximate subject 204 and configured to produce suitable MR pulse sequences when operated. Primary receive coil 202 may be a single coil or may be a plurality of coils, which, in the latter case, may be used to perform parallel MRI. Tuning circuitry 208 facilitates operation of primary receive coil 202 and signals detected by RF coil(s) 202 are provided to acquisition system 210, which may amplify the detected signals, digitize the detected signals, and/or perform any other suitable type of processing.

Transmit/receive system 200 also includes auxiliary sensor(s) 206, which may include any number or type of sensor(s) configured to detect or otherwise measure noise sources in the environment and/or environmental noise produced by the MRI system itself. The noise measured by auxiliary sensor(s) 206 may be characterized and used to suppress noise in the MR signal detected by primary RF coil(s) 202 using techniques described in further detail below. After acquisition system 210 processes the signals detected by RF coil(s) 202 and auxiliary sensor(s) 206, acquisition system 210 may provide the processed signals to one or more other components of the MRI system for further processing (e.g., for use in forming one or more MR images of subject 204). Acquisition system 210 may comprise any suitable circuitry and may comprise, for example, one or more controllers and/or processors configured to control the MRI system to perform noise suppression in accordance with embodiments described herein. It should be appreciated that components illustrated in FIG. 2 may be configured to detect MR signals generated by any suitable MRI system including any MRI system described in U.S. Pat. No. 10,222,434, dated Mar. 5, 2019, titled "Portable Magnetic Resonance Imaging Methods and Apparatus," which is herein incorporated by reference in its entirety.

Figure 3:
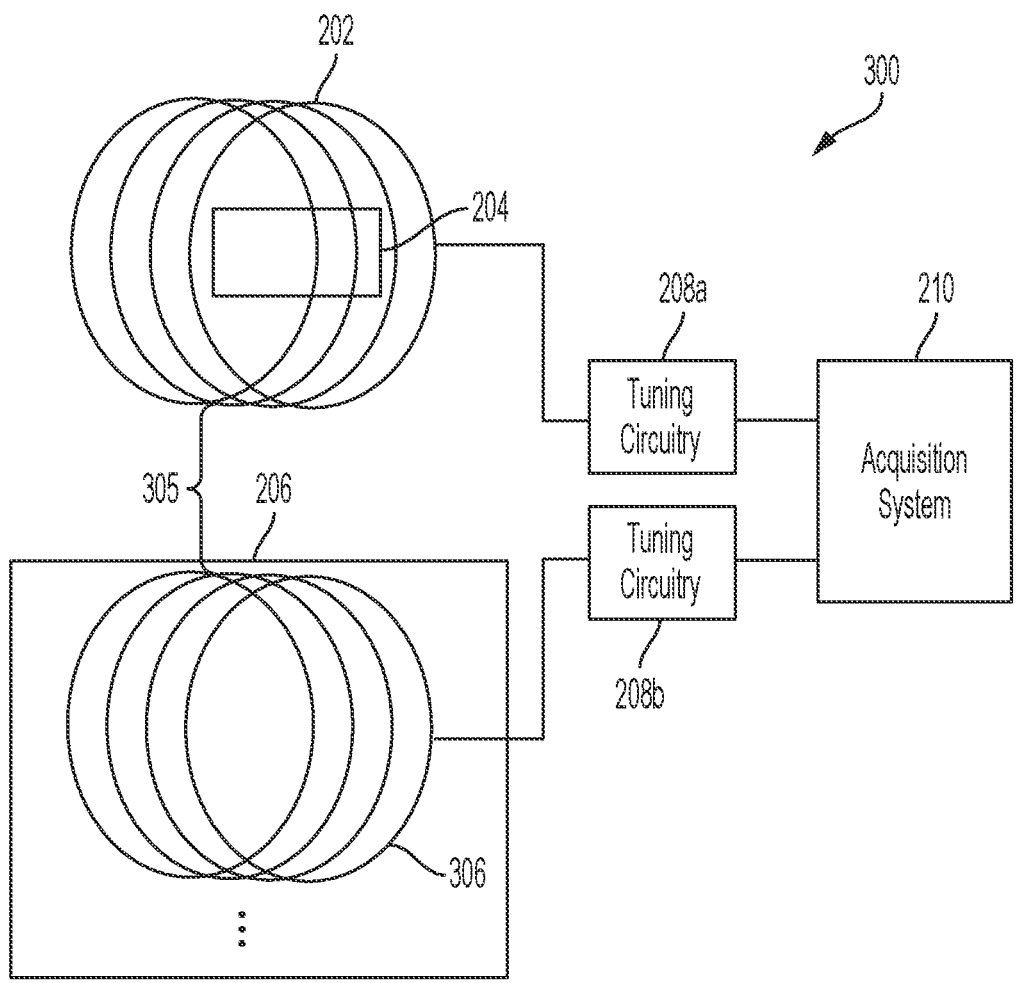
FIG. 3 illustrates exemplary components of an MRI system used for performing noise suppression, in accordance with some embodiments of the technology described herein.

In some embodiments, auxiliary sensor(s) 206 may include one or more auxiliary coils 306 configure to measure noise from one or more noise sources in the environment in which the MRI system is operating, as shown in FIG. 3. In some instances, the auxiliary RF coil(s) 306 may be constructed to be substantially more sensitive to ambient noise than to any noise generated by the coil itself. For example, the auxiliary RF coil 306 may have a sufficiently large aperture and/or a number of turns such that the auxiliary coil is more sensitive to noise from the environment than to noise generated by the auxiliary coil itself. In some embodiments, auxiliary RF coil(s) 306 may have a larger aperture and/or a greater number of turns than primary RF coil(s) 202. However, auxiliary RF coil(s) 306 may be the same as primary RF coil in this respect and/or may differ from primary RF coil(s) 202 in other respects, as the techniques described herein are not limited to any particular choice of coils. For example, in some embodiments, an auxiliary sensor of a different type is used in place of an RF coil type sensor, as discussed in further detail below.

In the illustrative embodiment of FIG. 3, auxiliary RF coil(s) 306 is/are located a distance 305 apart from primary RF coil 202. The distance 305 may be selected such that auxiliary coil(s) 306 is/are sufficiently far away from the sample 204 to avoid sensing MR signals emitted by the sample during imaging, but otherwise arranged as close as possible to the primary RF coil 202 so that auxiliary coil(s) 306 detect noise similar to the noise detected by primary coil(s) 202. In this manner, the noise from one or more noise sources measured by auxiliary coil(s) 306 and characterized using techniques discussed herein (e.g., by using the detected noise to calculate, at least in part, a transform that can be used to suppress and/or eliminate noise present on detected MR signals) may be representative of the noise detected by primary coil(s) 202. It should be appreciated that auxiliary coil(s) 306 need not be RF coils, but may be any type of sensor capable of detecting or measuring noise in the environment that may impact the performance of the MRI system, as the techniques described herein are not limited for use with any particular type of sensor.

Figure 4:
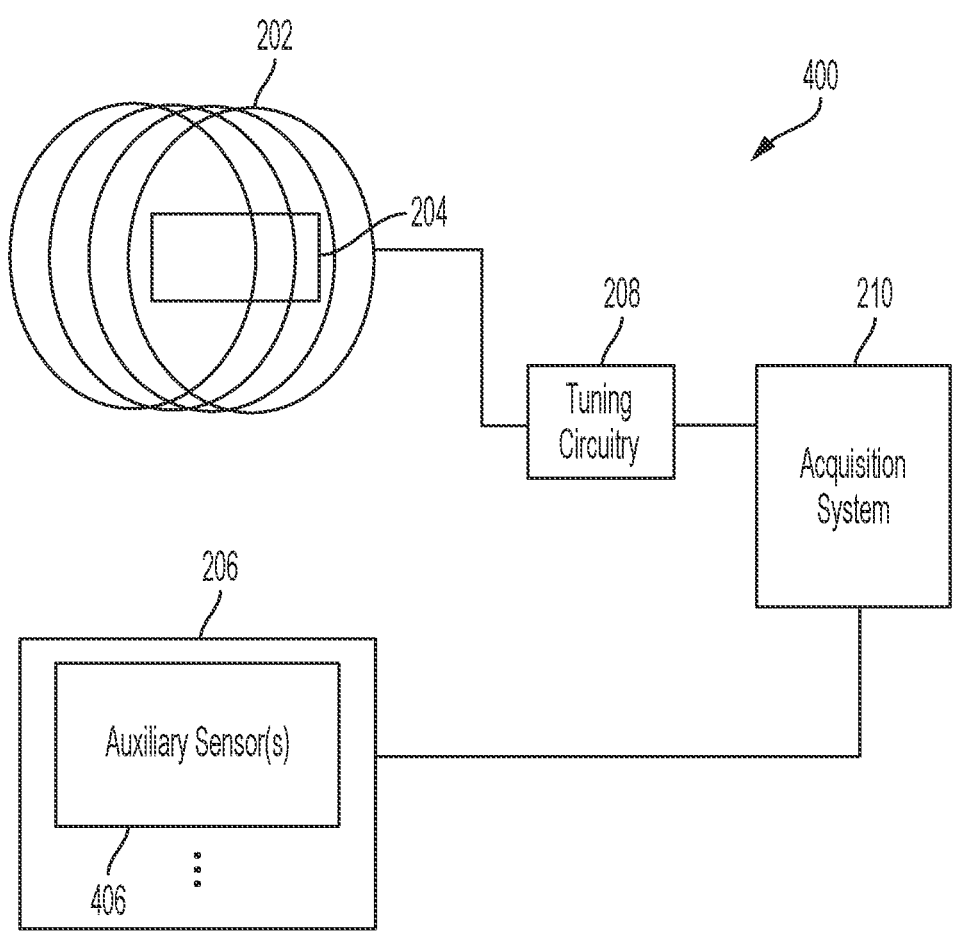
FIG. 4 illustrates exemplary components of an MRI system used for performing noise suppression, in accordance with some embodiments of the technology described herein.

According to some embodiments, auxiliary sensor(s) 206 may include one or more auxiliary sensors 406 configure to measure noise by coupling sensor(s) to one or more components of the MRI system, as schematically shown in FIG. 4. For example, auxiliary sensors 406 may include one or more sensors coupled to one or more components of the MRI system or otherwise arranged to detect noise produced by the MRI system. As discussed above, power cables are frequently a source of noise that can have a negative impact on the operation of the MRI system and, in particular, may produce noise that is detected by the one or more primary coils. According to some embodiments, auxiliary sensor(s) 406 include one or more sensors coupled (e.g., capacitively or inductively) to one or more power cables of the system to detect noise produced therefrom. The detected noise may be characterized and used to suppress noise from detected MR signals, for example, by using the detected noise to produce, at least in part, a transform that characterizes noise detected by the auxiliary sensor(s) 406, or by being directly applied to detected MR signals.

As discussed above, the low-field regime may facilitate systems that can be utilized in a wide variety of circumstances and/or that can be generally transported from one location to another. As a result, low-field MRI systems will frequently operate outside of specially shielded rooms. Thus, some low-field MRI systems may utilize partial shielding of one or more components of the system to prevent at least some EMI from reaching the shielded components. The inventors have appreciated that by coupling one or more sensors to one or more EMI shields (e.g., a Faraday cage of one or more components or the like) of the system, the noise absorbed by the one or more EMI shields can be measured, characterized and used to suppress and/or eliminate noise from detected MR signals. According to some embodiments, auxiliary sensor(s) 406 include one or more sensors coupled between one or more EMI shields and ground to measure noise absorbed by the EMI shield that can be used to facilitate noise suppression. For example, the noise detected from the EMI shield may be used to compute, at least in part, a transform that can be utilized in suppressing and/or eliminating noise from detected MR signals. It should be appreciated that auxiliary sensor(s) 406 may include any other type of sensor capable of detecting noise, as the aspects are not limited in this respect.

Figure 5:
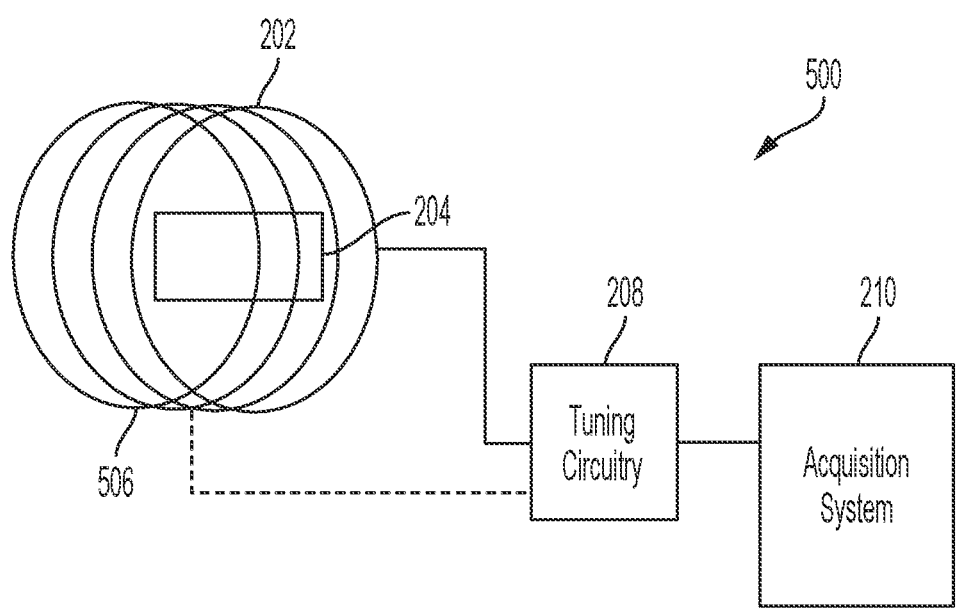
FIG. 5 illustrates exemplary components of an MRI system used for performing noise suppression, in accordance with some embodiments of the technology described herein.

According to some embodiments, auxiliary sensor(s) 206 include the primary coil(s) itself as illustrated in FIG. 5, wherein the primary RF coil(s) are labeled both as primary receive coil 202 and auxiliary sensor 506 for the system, as the primary RF coil(s) may perform both roles in some circumstances. As discussed above, the inventors have recognized that certain pulse sequences facilitate using the signals acquired from the primary coil(s) to also suppress noise thereon. A pulse sequence refers generally to operating transmit coil(s) and gradient coil(s) in a prescribed sequence to induce an MR response. By repeating the same pulse sequence using the same spatial encoding, "redundant" MR signals can be obtained and used to estimate noise present in the MR signals.

To address the relatively low signal-to-noise ratio (SNR) of low-field MRI, pulse sequences have been utilized that repeat MR data acquisitions using the same spatial encoding (e.g., by repeating a pulse sequence with the same operating parameters to drive the gradient coils in the same manner). The MR signals obtained over multiple acquisitions are averaged to increase the SNR. For example, a balanced steady-state free precession (bSSFP) pulse sequence may be used to rapidly obtain MR data over multiple acquisitions, which acquisitions are then averaged together to increase the SNR. The term "average" is used herein to describe any type of scheme for combining the signals, including absolute average (e.g., mean), weighted average, or any other technique that can be used to increase the SNR by combining MR data from multiple acquisitions. Because the bSSFP pulse sequence does not require waiting for the net magnetization to realign with the $B_0$ field between successive MR data acquisitions (e.g., successive acquisitions may be obtained without needing to wait for the transverse magnetization vector to decrease to 0), multiple acquisitions may be rapidly obtained. However, any pulse sequence can be used to perform multiple acquisitions at the same location, as the aspects are not limited in this respect.

The inventors have appreciated that the MR data obtained during multiple acquisitions performed using the same spatial encoding may be used to suppress and/or eliminate noise from the detected MR signal. As discussed above, when multiple acquisitions are performed by repeating the pulse sequence with the same spatial encoding, the MR signals obtained should be the same or nearly the same and the differences can be attributed to noise. As such, phase shifting the MR signal obtained over multiple acquisitions and computing the difference between the signals provides a means for evaluating the noise corrupting the MR data. The difference may be obtained by phase shifting and either adding or subtracting the phase shifted MR signals depending on the type of pulse sequence utilized. For example, the bSSFP pulse sequence flips the polarity of the pulse sequence on subsequent acquisitions so that the difference may be computed by adding MR signals that have been appropriately shifted in phase. However, MR signals obtained using other pulse sequences that do not flip the polarity may be subtracted after being appropriately phase shifted to obtain the difference between multiple MR acquisitions. Because multiple acquisitions (e.g., 10, 20, 50, 100, 150 or more) obtained using the same spatial encoding may already be performed (and averaged) in the low-field context to achieve sufficiently large SNR, using one or more of the acquisitions to compute a noise estimate will not substantially increase acquisition times, if at all.

The computed noise (e.g., the difference between MR signals obtained over multiple acquisitions with the same spatial encoding can be used to suppress and/or eliminate the noise in the detected MR signal. According to some embodiments, the noise computed according to the above described technique may be used to, at least in part, determine a transform that can be used to suppress and/or eliminate noise in the manner discussed in further detail below. However, noise computed by determining the difference between multiple MR acquisitions can be utilized in other ways to suppress and/or eliminate noise, as the aspects are not limited in this respect. For example, noise computed based on determining the difference between multiple MR acquisitions obtained from the same location may be directly applied to detected MR signals or applied after further processing. It should be appreciated that the noise computed by comparing multiple acquisitions obtained using the same spatial encoding can be used to dynamically suppress and/or eliminate noise from the detected MR signals. In this way, noise cancellation dynamically adapts to changing noise conditions in the environment.

As discussed above, noise detected by one or more auxiliary sensors, some examples of which are described in the foregoing, may be used to characterize the noise from one or more noise sources and suppress and/or eliminate noise from detected MR signals. According to some embodiments, the noise detected by one or more auxiliary sensors is used to determine a transform that can be used to transform detected noise to an approximation of the noise detected by the one or more primary receive coils. According to some embodiments, noise detected by one or more auxiliary sensors is applied to detected MR signals to suppress noise without using a transform.

As a non-limiting example, a noise suppression component (e.g., acquisition system 210 illustrated in FIGS. 2-5) may suppress noise in a signal $s_{pri}(t)$, detected by primary RF coil 202, by using the signal $s_{aux}(t)$, detected by auxiliary sensor 206, and a primary-to-auxiliary sensor (PA) transfer function $H_{PA}(\omega)$ via the following expression:

$$s_{comp}(t)=s_{pri}(t)-\mathcal{F}^{-1}\{H_{PA}(\omega)S_{aux}(\omega)\}, \quad (1)$$

where $S_{aux}(\omega)$ is the Fourier transform of $s_{aux}(t)$, $\mathcal{F}^{-1}\{\}$ is the inverse Fourier transform operator, and $s_{comp}(t)$ is the noise-suppressed signal. It should be appreciated that the noise compensation calculation of Equation (1) may be implemented in any of numerous ways and, for example, may be implemented in the frequency domain or in the time domain, as the noise suppression techniques described herein are not limited in this respect. Exemplary techniques for estimating a PA transfer function are described in more detail below.

Figure 6:
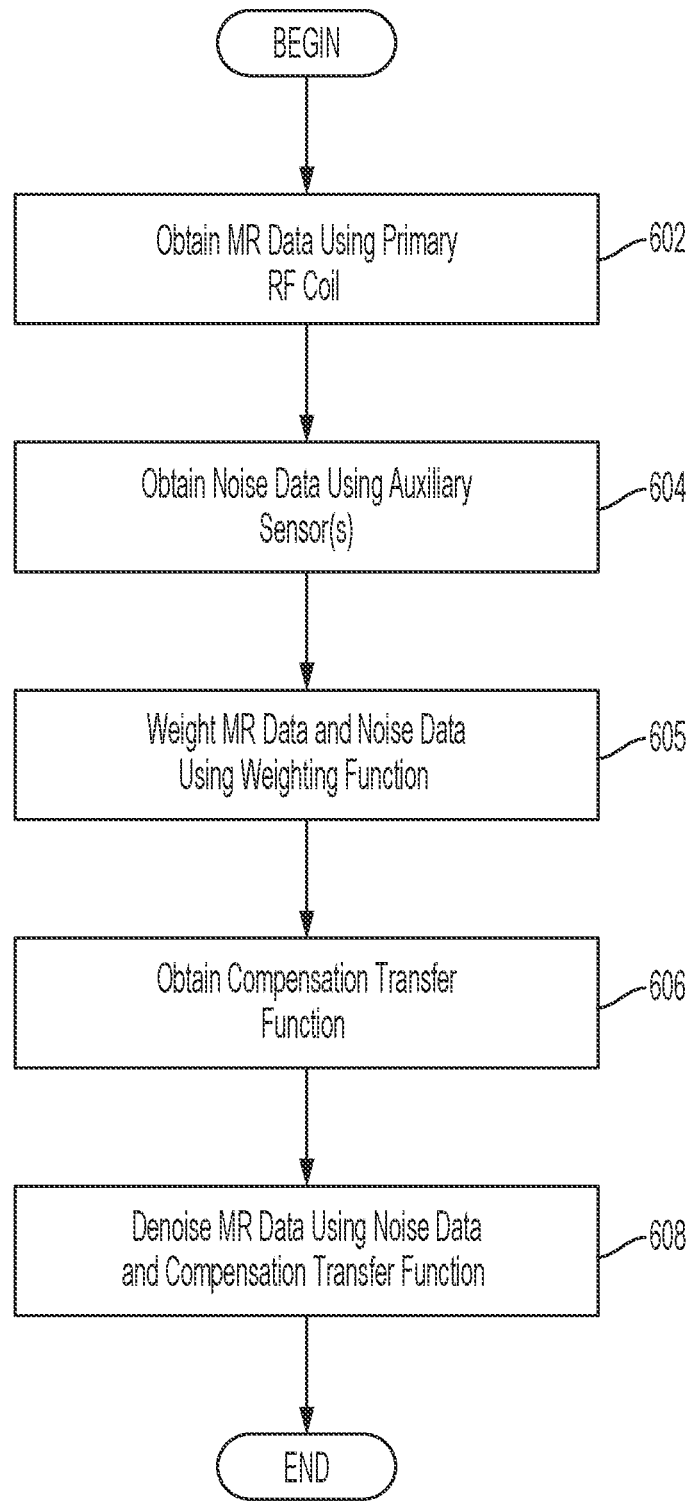
FIG. 6 is a flowchart of an illustrative process for performing noise suppression, in accordance with some embodiments of the technology described herein.

FIG. 6 is a flowchart of an illustrative process 600 for performing noise suppression, in accordance with some embodiments of the technology described herein, including a detailed description of a technique for determining an exemplary transfer function, first with respect to a transfer function between an auxiliary sensor and a primary receive coil, followed by a description of a transfer function between multiple auxiliary sensors and a primary receive coil (multichannel transfer function). It should be appreciated that a single or multi-channel transfer function may be computed for any number of receive coils so that noise cancellation in this respect can be performed using any number and type of auxiliary sensor and any number and type of receive coil. Process 600 may be performed by components of any suitable MRI system and, for example, may be performed by components of MRI system 100 described with reference to FIG. 1 and the associated components illustrated in FIGS. 2-5.

Process 600 begins at acts 602 and 604, where a MRI system obtains MR data by using a primary RF coil (e.g., RF coil 202) and obtains noise data using one or more auxiliary sensors (e.g., one or more RF coils 306 and/or one or more other sensors 206, 406, 506, etc.). As discussed above, any number of auxiliary sensors of any type may be used to characterize the noise in the environment of the MRI system. To illustrate aspects of the noise suppression techniques, the case of a primary RF coil and an auxiliary sensor is first considered. The primary RF coil and auxiliary sensor may operate to obtain MR and noise data substantially simultaneously such that the noise data acquired by the auxiliary sensor may be used to suppress noise in the MR data acquired by the primary RF coil.

The signal obtained by the primary RF coil may comprise both noise and an MR signal emitted by the sample being imaged. For example, if $s_{pri}(t)$ represents the total signal measured by the primary RF coil, then $s_{pri}(t)$ may be expressed as:

$$s_{pri}(t) = m_{pri}(t) + n_{pri}(t)$$

where $m_{pri}(t)$ and $n_{pri}(t)$ represent the MR signal and noise components of the total signal measured by the primary RF coil. Assuming that the auxiliary sensor measures a negligible amount of MR signal (due to the placement of the auxiliary sensor relative to the primary RF coil and the sample being imaged), the signal measured by the auxiliary sensor contains mostly ambient RF noise. For example, if $s_{aux}(t)$ represents the total signal measured by the auxiliary sensor, then $s_{aux}(t)$ may be expressed according to:

$$s_{aux}(t) = n_{aux}(t),$$

where $n_{aux}(t)$ is noise measured by the auxiliary sensor.

As discussed above, the noise components of the signals measured by the primary RF coil and auxiliary sensor may be different (e.g., $n_{pri}(t)$ may be different from $n_{aux}(t)$) due to physical differences between the primary coil and auxiliary sensor as well as differences in location and orientation. However, the inventors have appreciated that a relationship between the noise signals measured by the primary coil and the auxiliary sensor may be established since both measure noise from one or more common sources. Such a relationship may be, in some embodiments, represented by a primary to auxiliary transfer function $H_{PA}(\omega)$ as detailed below.

For example, in some embodiments, each of the noise signals $n_{pri}(t)$ and $n_{aux}(t)$ may contain noise from several independent sources including, but not limited to, noise from one or more sources in the environment of the low-field MRI system, noise generated by the primary RF coil and/or the auxiliary sensor, and noise generated by one or more other components of the MRI system (e.g., noise generated by tuning circuitry, acquisition system, power cables, etc.). Thus, for example, the noise signals $n_{pri}(t)$ and $n_{aux}(t)$ may be expressed as:

$$n_{pri}(t) = c_{pri}(t) + u_{pri}(t), \text{ and}$$

$$n_{aux}(t) = c_{aux}(t) + u_{aux}(t) \cong c_{aux}(t),$$

where $c_{pri}(t)$ and $c_{aux}(t)$ represent correlated noise (i.e., the signals $c_{pri}(t)$ and $c_{aux}(t)$ are correlated) generated by one or more common noise sources detected by the primary coil and the auxiliary sensor, respectively, and where $u_{pri}(t)$ and $u_{aux}(t)$ represent uncorrelated noise detected by the primary coil and auxiliary sensors, respectively (e.g., noise generated by the primary coil and auxiliary sensor themselves). As described above, in some embodiments, the auxiliary sensor may be configured such that it is more sensitive to noise from the environment than noise generated by the sensor itself. For example, the auxiliary sensor may be an auxiliary RF coil having a sufficiently large aperture and/or number of turns. As such, $c_{aux}(t)$ may be substantially larger than $u_{aux}(t)$ so that $n_{aux}(t) \cong c_{aux}(t)$.

Each of the noise signals $c_{pri}(t)$ and $c_{aux}(t)$ can be expressed in relation to the common noise source(s) through a respective measurement transfer function. For example, in the Fourier domain, the Fourier transforms $C_{pri}(\omega)$ and $C_{aux}(\omega)$ of noise signals $c_{pri}(t)$ and $c_{aux}(t)$ can be expressed as:

$$C_{pri}(\omega) = H_{pri}(\omega) C_s(\omega)$$

$$C_{aux}(\omega) = H_{aux}(\omega) C_s(\omega)$$

where $C_s(\omega)$ is the Fourier transform of a common noise source and $H_{pri}(\omega)$ and $H_{aux}(\omega)$ respectively represent the channel between the common noise source and the primary receive coil and auxiliary sensor. Combining the above equations yields:

$$C_{pri}(\omega) = H_{PA}(\omega) C_{aux}(\omega),$$

where $$H_{PA}(\omega) = \frac{H_{pri}(\omega)}{H_{aux}(\omega)},$$

is the primary-to-auxiliary transfer function.

Next, at act 605, the MR data obtained at act 602 and the noise data obtained at act 604 are weighted using a weighting function (sometimes referred to as an "apodization" function or a "tapering" function). The same weighting function may be used to weight the MR data and the noise data. In some embodiments, the weighting function may be applied to the MR data and the noise data in the spatial frequency domain (sometimes termed "k-space") such that the obtained signals are weighted in the spatial frequency domain prior to being transformed to the image domain. Examples of weighting functions are described herein including below with reference to FIGS. 7A-7C.

In some embodiments, the weighting function may be symmetric about a middle region (e.g., about a maximum value at or near the middle of interval on which the weighting function takes on non-zero values). In some embodiments, the weighting function may be a Gaussian weighting function, a step weighting function, or a linear weighting function. Other weighting functions may be used in other embodiments including, but not limited to, a raised-cosine function, a Hamming window, a Hanning window, a Bartlett window, a Welch window, a Blackman window, a Kaiser window, etc.

The inventors have recognized that techniques for removing noise from the environment of an MRI machine may be improved through the use of a weighting step, like described with respect to act 605 of process 600. In particular, the inventors have recognized that, as data for an MR image is acquired, the signal to noise ratio (the power of the MR signal relative to the power of the noise) varies throughout the acquisition. When the signal to noise ratio is high (which may occur, for example, during acquisition at or near the center of k-space, when forming echoes of a coherent signal, when acquiring signal with minimal spatial encoding for navigators or correction signals (for frequency, phase, motion, or eddy currents, for example)) there is a risk of finding a false correlation between the signal and noise, and removing signal rather than noise from the measured MR signals during imaging. This, in turn, creates artefacts in MR images reducing their quality and signal to noise ratio.

However, the inventors have recognized that in MRI sequences, it is possible to predict which signal acquisitions are likely to have a high signal to noise ratio, and they can either be removed or suppressed by weighting (by zero or a non-zero weight, respectively) during the estimation of correlation between signals and noise (e.g., during estimation of a transfer function between the primary and auxiliary coils during act 606 of process 600). Accordingly, in some embodiments, the data obtained at acts 602 and 604 may be weighted in spatial-frequency regions determined to likely contain a high signal to noise ratio during imaging. For example, in some embodiments, the data obtained at acts 602 and 604 may be weighted in the spatial frequency domain to remove or suppress regions of k-space (e.g., middle of k-space) that are likely to contain a high signal to noise ratio during imaging. In this way, the transfer function estimated using these data will not, when used to suppress noise in MR signals during imaging of a patient, erroneously remove signal (instead of noise) and introduce undesirable artefacts. In some embodiments, the weighting function may be pre-defined based on the k-space encoding or the weighting function may be adaptively defined.

As another example, in some embodiments, the data obtained at acts 602 and 604 may be weighted to remove or suppress data below a pre-determined encoding threshold, including navigator or other types of signal correction acquisitions. The threshold may be determined adaptively based on the noise level. In some embodiments, a weighting function may specified in advance or dynamically determined within individual signal acquisitions.

Figure 7A:
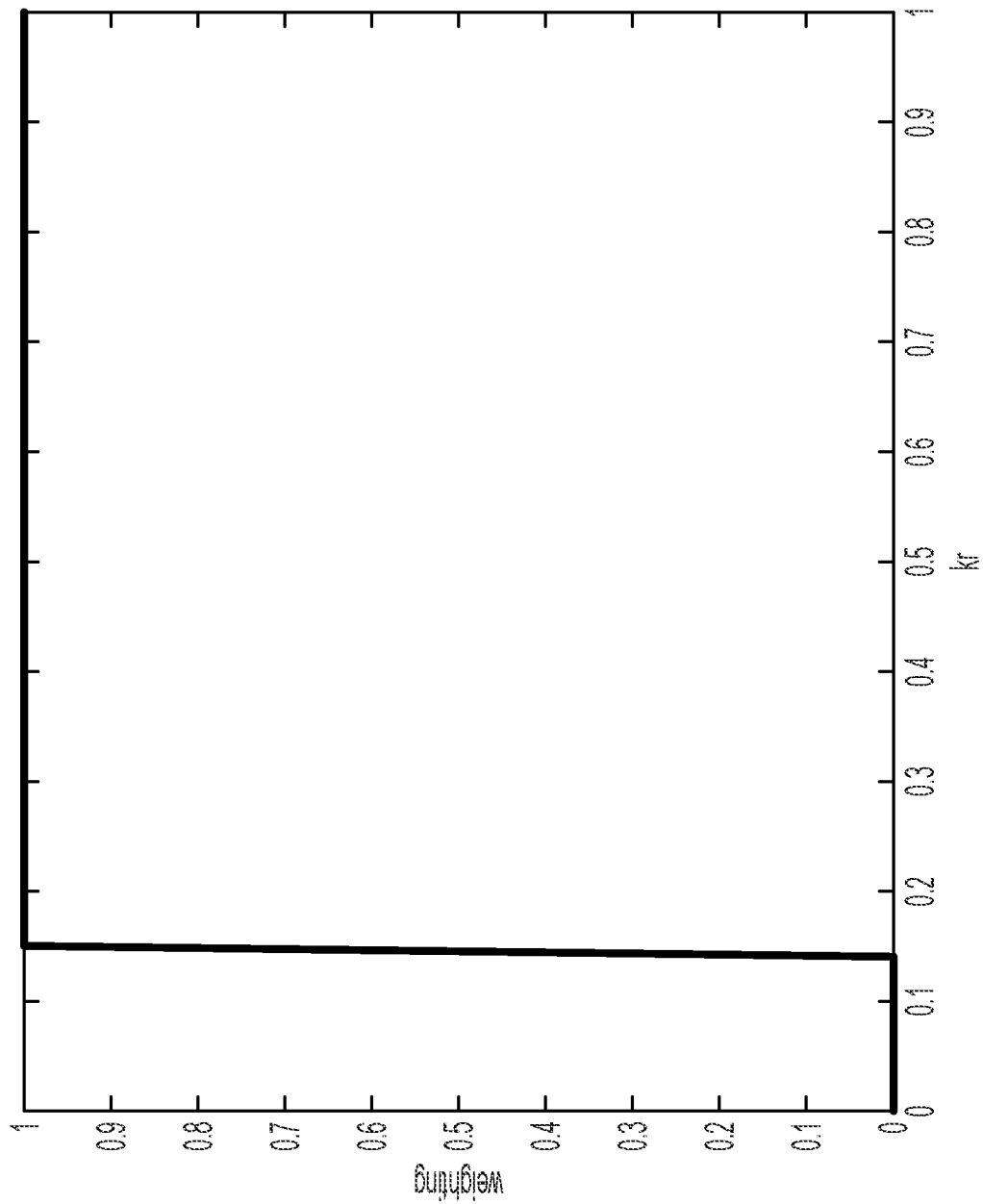
FIG. 7A is a diagram of an illustrative step weighting function, in accordance with some embodiments of the technology described herein.

As described above, in some embodiments, a step weighting function may be used. Let kr denote position in the spatial frequency domain (k-space). Generally, kr is encoded by gradients as $k_r = \gamma \int_0^t G(r, t)dt$, where $\gamma$ is the gyromagnetic ratio, r is an arbitrary spatial direction, t is time. G(r, t) is an arbitrary gradient waveform. Then the step weighting function may be defined according to:

$$\text{Weighting} = \begin{cases} 0, & kr < k_{thresh} \\ 1, & kr \geq k_{thresh} \end{cases}$$

where $k_{thresh}$ is a threshold below which MR and noise data obtained at acts 602 and 604 would be zeroed out, and as a result would be excluded from being used for estimating the transfer function at act 606. An illustrative plot of an example step weighting function in k-space is shown in FIG. 7A.

In some embodiments, a linear weighting function may be used. In this case, the weighting function may be defined according to:

Weighting=kr.

Figure 7B:
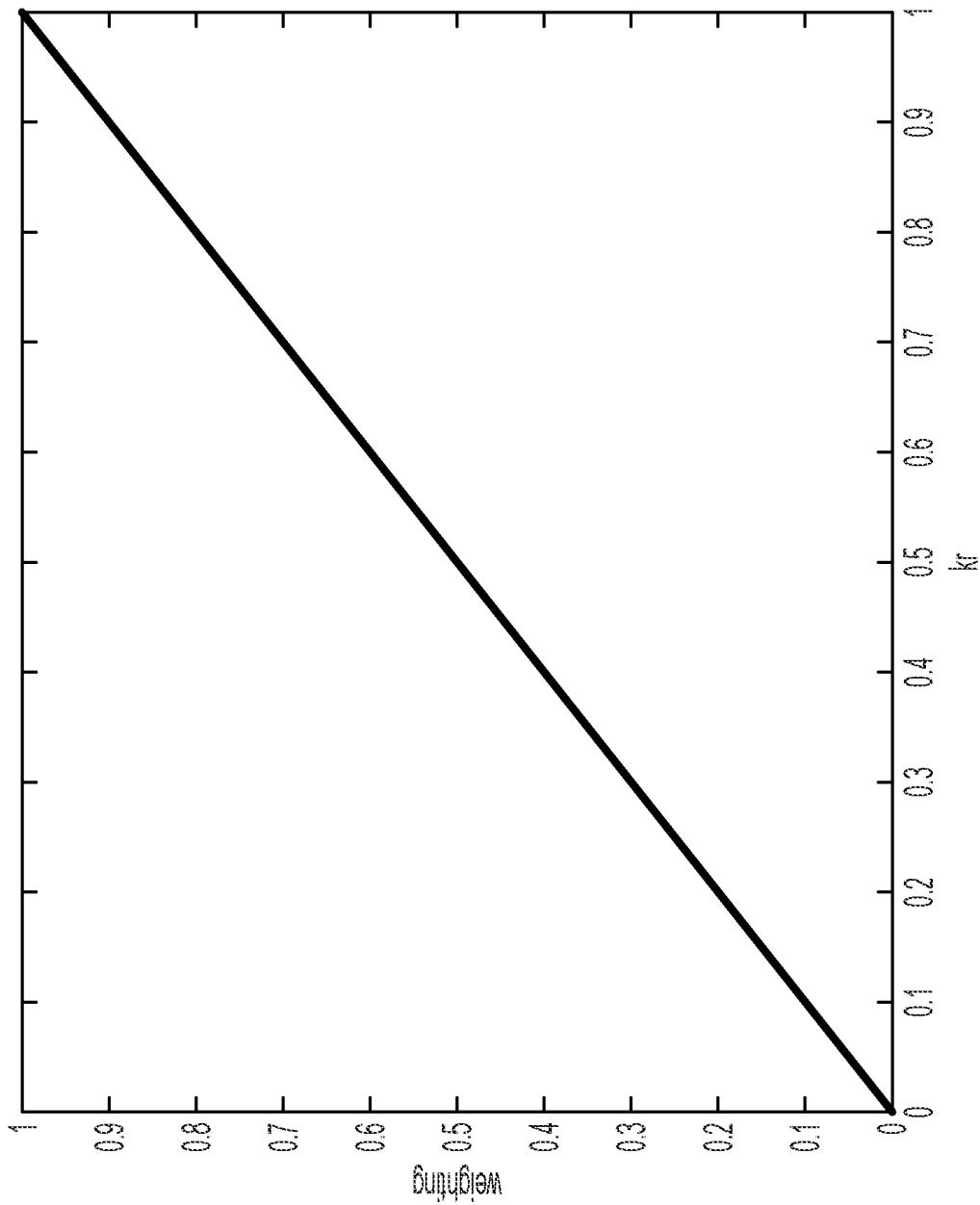
FIG. 7B is a diagram of an illustrative linear weighting function, in accordance with some embodiments of the technology described herein.

An illustrative plot of an example linear weighting function in k-space is shown in FIG. 7B.

Figure 7C:
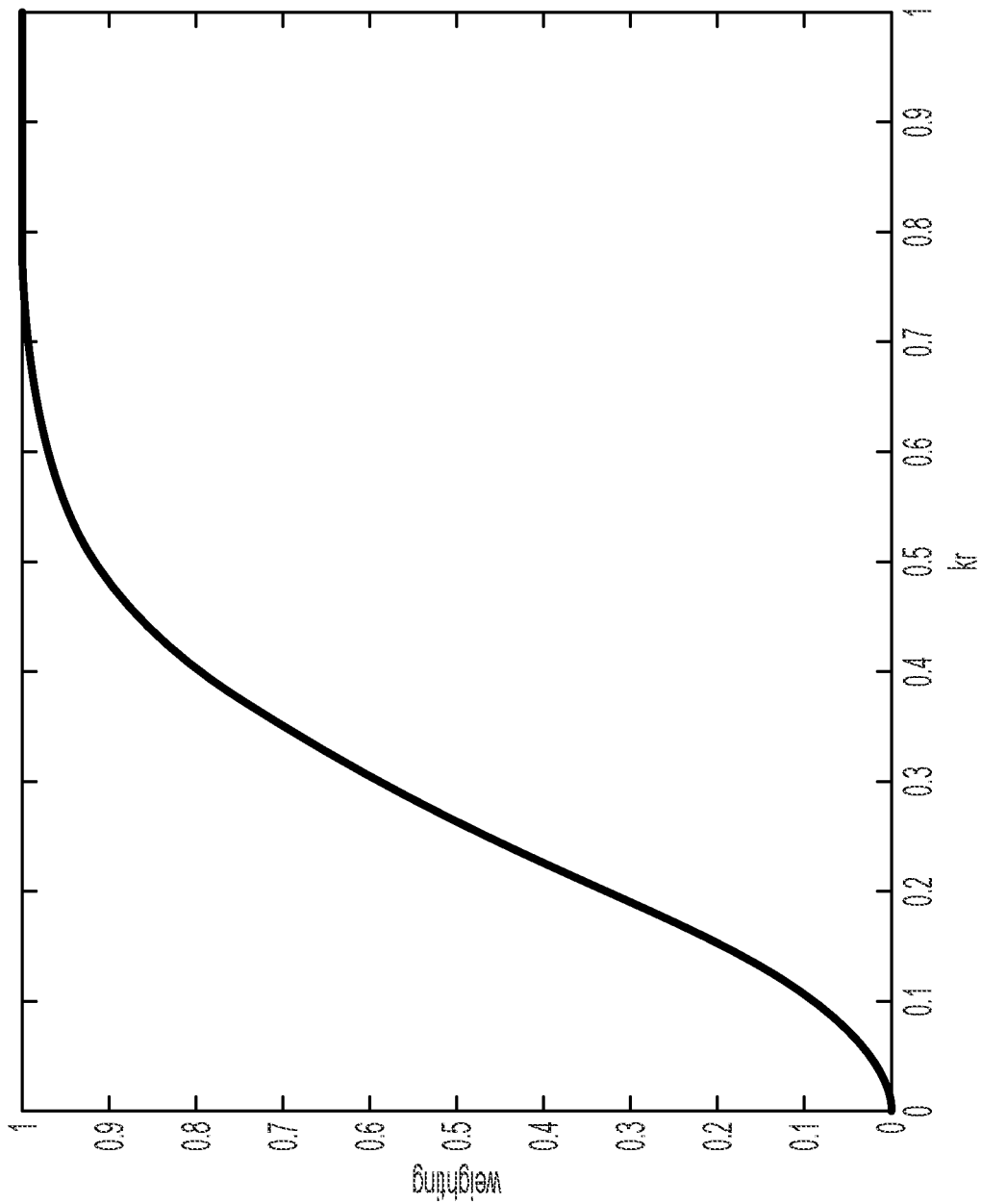
FIG. 7C is a diagram of an illustrative Gaussian weighting function, in accordance with some embodiments described herein.

In some embodiments, a Gaussian weighting function may be used. In some embodiments, the Gaussian weighting function may be scaled to 0 at regions where the highest signal to noise ratio is expected within an acquisition, and to 1 at regions where the lowest signal to noise ratio is expected within an acquisition. For example, in some embodiments, the Gaussian weighting function may be defined according:

Weighting=$1-e^{(-A*k_r2)}$, where A represents constant controlling the steepness of the Gaussian weighting function. An illustrative plot of an example Gaussian weighting function in k-space is shown in FIG. 7C.

In some embodiments, the weighting function may be estimated at act 605. For example, the parameter $k_{thresh}$ of the step-wise weighting function or the parameter A of the Gaussian weighting function may be estimated based on data gathered during acts 602 and 604. In other embodiments, the weighting function may be estimated prior to the start of process 600.

Returning to the discussion of process 600, after the MR and noise signals are acquired at acts 602 and 604 and the weighting is performed at act 605, process 600 proceeds to act 606, where a primary-to-auxiliary (PA) transfer function is obtained. In some embodiments, the PA transfer function may have been previously estimated so that obtaining the PA transfer function at act 606 comprises accessing a representation of the PA transfer function (e.g., a frequency-domain or a time-domain representation of the PA transfer function). In other embodiments, obtaining the PA transfer function at act 606 may comprise estimating and/or updating the estimate of the transfer function. Techniques for estimating a PA transfer function are described in more detail below.

Next, at act 608, the noise data obtained at act 604 and the PA transfer function obtained at act 606 may be used to suppress or cancel noise in the MR data obtained at act 602. This may be done using Equation (1) described above, using any equivalent formulation of Equation (1) (e.g., the entire calculation may be performed in the frequency domain), or in any other suitable way.

As described above, a primary-to-auxiliary transfer function may be used to suppress noise in the MR data acquired by a primary RF coil in a MRI system such as a low-field MRI system. In some embodiments, the primary-to-auxiliary transfer function may be estimated from calibration measurements obtained by the primary RF coil and the auxiliary sensor. This may be done in any suitable way. For example, the PA transfer function may be estimated from calibration measurements obtained when no MR signal is present or when the strength of the MR signal is small relative to the strength of the noise detected by the primary RF coil. As another example, the PA transfer function may be estimated from calibration measurements obtained when an MR signal is present (e.g., during operation of the MRI system). Any suitable number of calibration measurements may be used (e.g., at least 100, 100-1000, at least 1000, etc.). When more measurements are used, the PA transfer function may be estimated at a higher resolution (e.g., at more frequency values) and/or with increased fidelity with respect to the actual noise environment. The PA transfer function may be estimated using a least-squares estimation technique or any other suitable estimation technique, as the techniques described herein are not limited to any particular computational method.

As one non-limiting example, when the signal acquired by the primary coil at times $\{t_k\}$ does not contain any MR signal or when the strength of the MR signal is small relative to the strength of the noise detected by the primary RF coil, then $s_{pri}(t_k)=n_{pri}(t_k)$, so that the discrete Fourier transform of $s_{pri}(t_k)$ is given by:

$$S_{pri}(\omega_k)=C_{pri}(\omega_k)+U_{pri}(\omega_k),\qquad(1)$$

where $C_{pri}(\omega_k)$ is the discrete Fourier transform of $C_{pri}(t_k)$ and $U_{pri}(\omega_k)$ is the discrete Fourier transform of $u_{pri}(t_k)$. Since $C_{pri}(\omega_k)=H_{PA}(\omega_k)S_{ref}(\omega_k)$, the discrete Fourier transform of the signal received at the primary coil may be represented as a function of the discrete Fourier transform of the signal received at the auxiliary sensor according to:

$$S_{pri}(\omega_k)=H_{PA}(\omega_k)S_{aux}(\omega_k)+U_{pri}(\omega_k)\qquad(2)$$

Equation (2) represents a set of independent equations, one for each frequency component, $\omega_k$. Since both $U_{pri}$ and $H_{PA}$ are unknown, it may not be possible to determine $H_{PA}$ from a single calibration measurement. If M calibration measurements (e.g., at least 10, at least 100, at least 1000 calibration measurements) are made such that multiple examples of $S_{pri}$ and $S_{aux}$ for each frequency component are obtained, then the PA transfer function can be determined despite the unknown $U_{pri}$, via any suitable estimation technique, for example, via least squares estimation. This is so because multiple measurements may be used to average out the uncorrelated noise. Given M calibration measurements, a least squares estimator for the PA transfer function may be obtained by considering the following matrix equation for each frequency component $\omega_k$, $$\begin{bmatrix} S_{pri}(\omega_k)_1 \\ \vdots \\ S_{pri}(\omega_k)_M \end{bmatrix} = H_{PA}(\omega_k) \begin{bmatrix} S_{aux}(\omega_k)_1 \\ \vdots \\ S_{aux}(\omega_k)_M \end{bmatrix},$$

which can be solved according to:

$$H_{PA}(\omega_k) = \left\{ \begin{bmatrix} S_{aux}(\omega_k)_1 \\ \vdots \\ S_{aux}(\omega_k)_M \end{bmatrix}^T \begin{bmatrix} S_{aux}(\omega_k)_1 \\ \vdots \\ S_{aux}(\omega_k)_M \end{bmatrix} \right\}^{-1} \begin{bmatrix} S_{aux}(\omega_k)_1 \\ \vdots \\ S_{aux}(\omega_k)_M \end{bmatrix}^T \begin{bmatrix} S_{pri}(\omega_k)_1 \\ \vdots \\ S_{pri}(\omega_k)_M \end{bmatrix}.$$

As may be appreciated from the foregoing, the above-described estimator uses multiple measurements (i.e., M noise signals measured by each of the primary and auxiliary coils) to estimate the value of the primary-to-auxiliary transfer function for multiple frequency bins. This results in significantly improved estimates of the PA transfer function as compared to techniques which rely on a single measurement (i.e., a single signal measured by each of the primary and auxiliary coils) to estimate the transfer function. Such single-measurement techniques may include scaling and time-shifting the reference signal before subtraction, which would correct for a difference in phase between the noise signal as received at a primary coil and an auxiliary coil, but (unlike the multiple measurement technique described herein) would not correct for frequency-dependent phase differences.

Another single-measurement technique may include scaling and phase adjusting the auxiliary noise signal in the frequency domain before subtracting it from the signal received at the primary coil. This could be accomplished by using the discrete Fourier transform (DFT) of the signals received by a primary coil and an auxiliary coil. The optimal scaling and phase shift can be determined by a least-squares fit across multiple frequency bins. For example, if $S_{pri}(\omega_k)$ is the DFT of the signal measured on the primary receive coil and $S_{aux}(\omega_k)$ is the DFT of the signal measured on an auxiliary coil at the same time, an average scaling and phase shift SPF for a subset of frequency bins (in the range of [k1,k2]) may be computed according to:

$$SPF = \frac{\sum_{k1}^{k2} S_{aux}(\omega_k) S_{pri}(\omega_k)}{\sum_{k1}^{k2} S_{aux}(\omega_k) S_{aux}(\omega_k)}.$$

Although this single-measurement technique may be used to create a frequency-dependent correction, the method requires a tradeoff between frequency resolution of the correction and accuracy of the estimation of the scaling and phase offset. In particular, this "averaging across frequency bins of a single measurement" technique results in poor (e.g., high-variance, biased) estimation of a PA transfer function. In contrast, the above-described multiple measurement technique provides for an unbiased and low-variance estimator.

As described above, the inventors have appreciated that the use of multiple coils may facilitate improved MRI in a number of ways, including more robust noise detection and/or cancellation, accelerated image acquisition, etc. In embodiments where multiple primary receive coils and/or multiple auxiliary sensors are used, all of the sensors may be the same type or may be of different types. For example, in circumstances where one or more RF coils are used as sensors, none, some, or all of the coils may be shielded. As another example, the coils can have different sensitivities. When other types of sensors are used, at least some of the characteristics of the sensors and the primary receive coil(s) may necessarily be different, though some may be similar or the same.

In some embodiments, multiple auxiliary RF coils and/or primary RF coils may be used to accelerate imaging. For example, multiple RF coils used to sense noise from the same or different noise sources may also be used to perform parallel MR. In this manner, multiple RF coils may provide both noise characterization functions as well as accelerated image acquisition via their use as parallel receive coils.

In some embodiments, as described above, multiple sensors may be used to perform noise compensation in the presence of multiple noise sources. In an environment having N correlated noise sources, where N is an integer greater than one, the Fourier transforms $C_{pri}(\omega)$ and $C_{aux}(\omega)$ of noise signals $c_{pri}(t)$ and $c_{aux}(t)$, received by a primary coil and an auxiliary sensor can be expressed as:

$$C_{pri}(\omega)=H_{pri,1}(\omega)C_1(\omega)+H_{pri,2}(\omega)C_2(\omega)+\ldots+H_{pri,N}(\omega)C_N(\omega)$$

$$C_{aux}(W)=H_{aux,1}(\omega)C_1(\omega)+H_{aux,2}(\omega)C_2(\omega)+\ldots+H_{aux,N}(\omega)C_N(\omega),$$

where $C_j(\omega)$; $1 \leq j \leq N$, is a Fourier transform of a noise signal from the jth noise source, $H_{pri,j}(\omega)$ is a transfer function between the primary coil and the jth noise source, and $H_{aux,j}(\omega)$ is a transfer function between the auxiliary sensor and the jth noise source. When the ratio $H_{pri,j}(\omega)/H_{aux,j}(\omega)$ is different for one or more noise sources, it may not be possible to perform high quality noise compensation by using only a single auxiliary sensor. However, multiple auxiliary sensors may be used to perform noise compensation in this circumstance as described below.

Described below is a non-limiting example of how multiple auxiliary sensors may be used to perform noise compensation for multiple different noise sources. Without loss of generality, suppose a MR system has a primary coil and P auxiliary sensors (where P is any integer greater than or equal to 1). Further, suppose that the MR system is deployed in an environment in which there are N different noise sources (where N is an integer greater than or equal to 1). Let $H_{ij}(\omega)$ denote the transfer function between the ith auxiliary sensor (where $1 \leq i \leq P$) and the jth noise source (where $1 \leq j \leq N$). The following set of equations relate the Fourier transforms of the signals received by the auxiliary sensors to the Fourier transforms of the noise signals produced by the noise sources:

$$\begin{bmatrix} H_{11} & \cdots & H_{1N} \\ \vdots & \ddots & \vdots \\ H_{P1} & \cdots & H_{PN} \end{bmatrix} \begin{bmatrix} C_1 \\ \vdots \\ C_N \end{bmatrix} = \begin{bmatrix} C_{aux,1} \\ \vdots \\ C_{aux,P} \end{bmatrix},$$

where $C_{aux,i}$; $1 \leq i \leq P$, is a Fourier transform of the signal received at the ith auxiliary sensor, $C_j(\omega)$; $1 \leq j \leq N$ is a Fourier transform of a noise signal from the jth noise source, and where the dependence of all the terms on frequency is not shown explicitly (the ($\omega$) is suppressed for brevity), though it should be appreciated that all the terms in the above matrix equation are functions of frequency.

When the number of auxiliary sensors is greater than or equal to the number of noise sources (i.e., P>=N), the above matrix equation may be solved for the noise signals according to:

$$\begin{bmatrix} C_1 \\ \vdots \\ C_N \end{bmatrix} = \left\{ \begin{bmatrix} H_{11} & \cdots & H_{1N} \\ \vdots & \ddots & \vdots \\ H_{P1} & \cdots & H_{PN} \end{bmatrix}^T \begin{bmatrix} H_{11} & \cdots & H_{1N} \\ \vdots & \ddots & \vdots \\ H_{P1} & \cdots & H_{PN} \end{bmatrix} \right\}^{-1} \begin{bmatrix} H_{11} & \cdots & H_{1N} \\ \vdots & \ddots & \vdots \\ H_{P1} & \cdots & H_{PN} \end{bmatrix}^T \begin{bmatrix} C_{aux,1} \\ \vdots \\ C_{aux,P} \end{bmatrix}.$$

If such a solution exists, the correlated noise measured on the primary receive coil may be expressed in relation to the measurements obtained by all of the auxiliary sensors according to:

$$C_{pri} = [H_{pri,1} \cdots H_{pri,N}]$$

$$\left\{ \begin{bmatrix} H_{11} & \cdots & H_{1N} \\ \vdots & \ddots & \vdots \\ H_{P1} & \cdots & H_{PN} \end{bmatrix}^T \begin{bmatrix} H_{11} & \cdots & H_{1N} \\ \vdots & \ddots & \vdots \\ H_{P1} & \cdots & H_{PN} \end{bmatrix} \right\}^{-1} \begin{bmatrix} H_{11} & \cdots & H_{1N} \\ \vdots & \ddots & \vdots \\ H_{P1} & \cdots & H_{PN} \end{bmatrix}^T \begin{bmatrix} C_{aux,1} \\ \vdots \\ C_{aux,P} \end{bmatrix}$$

A multi-channel transfer function $H_{MPA}$ may be defined according to:

$$H_{MPA} = [H_{PA,1} \cdots H_{PA,P}] = [H_{pri,1} \cdots H_{pri,N}]$$

$$\left\{ \begin{bmatrix} H_{11} & \cdots & H_{1N} \\ \vdots & \ddots & \vdots \\ H_{P1} & \cdots & H_{PN} \end{bmatrix}^T \begin{bmatrix} H_{11} & \cdots & H_{1N} \\ \vdots & \ddots & \vdots \\ H_{P1} & \cdots & H_{PN} \end{bmatrix} \right\}^{-1} \begin{bmatrix} H_{11} & \cdots & H_{1N} \\ \vdots & \ddots & \vdots \\ H_{P1} & \cdots & H_{PN} \end{bmatrix}^T.$$

It may then be seen that the noise measured by the primary receive coil is a linear combination of the noise signals measured on all the auxiliary coils:

$$C_{pri} = [H_{PA,1} \cdots H_{PA,P}] \begin{bmatrix} C_{aux,1} \\ \vdots \\ C_{aux,P} \end{bmatrix}. \quad (3)$$

Thus, given noise signals measured by P auxiliary sensors (e.g., the Fourier transforms of which are given by $C_{aux,i}$ for $1 \leq i \leq P$), the above equation may be used to estimate the noise signal received at the primary receive coil (e.g., the Fourier transform of which is given by $C_{pri}$). In turn, the estimated noise signal may be subtracted from the overall signal measured by the primary receive coil (which signal would have both an MR signal component and a noise component) to perform noise suppression.

However, to use the above equation (3), an estimate of the multichannel primary-to-auxiliary transfer function $H_{MPA} = [H_{PARC,1} \cdots H_{PARC,P}]$ is needed. This may be achieved in any suitable way and, in some embodiments, may be done by making multiple measurements using the primary receive coil and the auxiliary sensors (e.g., at a time when there is no MR signal present) and using these measurements to estimate the multichannel primary-to-auxiliary transfer function. For example, given M measurements of noise signals at each of the P auxiliary sensors and the primary receive coil, the $H_{MPA}$ may be estimated for each frequency component $\omega_k$ (where k is an index over frequency bins) using least squares estimation according to:

$$\begin{bmatrix} H_{PA,1}(\omega_k) \\ \vdots \\ H_{PA,P}(\omega_k) \end{bmatrix} =$$

$$\left\{ \begin{bmatrix} S_{aux,1}(\omega_k)_1 & \cdots & S_{aux,P}(\omega_k)_1 \\ \vdots & \ddots & \vdots \\ S_{aux,1}(\omega_k)_M & \cdots & S_{aux,P}(\omega_k)_M \end{bmatrix}^T \begin{bmatrix} S_{aux,1}(\omega_k)_1 & \cdots & S_{aux,P}(\omega_k)_1 \\ \vdots & \ddots & \vdots \\ S_{aux,1}(\omega_k)_M & \cdots & S_{aux,P}(\omega_k)_M \end{bmatrix} \right\}^{-1} \times$$

$$\begin{bmatrix} S_{aux,1}(\omega_k)_1 & \cdots & S_{aux,P}(\omega_k)_1 \\ \vdots & \ddots & \vdots \\ S_{aux,1}(\omega_k)_M & \cdots & S_{aux,P}(\omega_k)_M \end{bmatrix}^T \times \begin{bmatrix} S_{pri}(\omega_k)_1 \\ \vdots \\ S_{pri}(\omega_k)_M \end{bmatrix},$$

where $S_{aux,i}(\omega_k)_m$ represents the value of the kth frequency bin of the Fourier transform of the mth measured signal obtained by the ith auxiliary sensor, and where $S_{pri}(\omega_k)_m$ represents the value of the kth frequency bin of the Fourier transform of the mth measured signal obtained by the primary receive coil. This least-squares approach provides the most complete correction when the columns of the following matrix are as orthogonal as possible to one another:

$$\begin{bmatrix} H_{11} & \cdots & H_{1N} \\ \vdots & \ddots & \vdots \\ H_{P1} & \cdots & H_{PN} \end{bmatrix}.$$

Put another way, each auxiliary sensor may detect some or all of the different noise sources in a unique way from other auxiliary sensors. In order to correct for the presence of near field sources, multiple sensors may be placed in different locations to be more or less sensitive to some of the noise sources. In some embodiments, multiple sensors may be oriented orthogonally to one another (e.g., one sensor may be oriented in an "X" direction, another sensor may be oriented in the "Y" direction, and another sensor may be oriented in a "Z" direction). In this way, each vector of the time varying interference fields may be captured. It may also be beneficial to use one or more antennas as an auxiliary sensor to provide another orthogonal measurement.

It should be appreciated that although some of the embodiments described herein involve estimating the correlation between signal and noise channels using time-domain or Fourier domain calculations, this is not a limitation of the technology described herein. In some embodiments, the correlation between the signal and noise channels (e.g., between the signals obtained by one or more primary RF coils and one or more auxiliary RF coils) may be determined using other techniques including, but not limited to, wavelet correlation, independent components analysis (ICA), principal components analysis (PCA), blind source separation, etc. Regardless of the technique employed, however, weighting the data to focus on regions dominated by noise (rather than on signals dominated by signal) will improve the quality of the estimate of the correlation between the signal and noise data and reduce artefacts in MRI images obtained by suppression noise based on such a correlation estimate.

It should also be appreciated that the weighting techniques described herein may be used to generate an expanded set of virtual coils for signal or noise.

It should be appreciated that the techniques described herein facilitate detecting noise in the environment of an MRI system using any number and/or type of sensor suitable for detecting noise produced by respective noise sources. As a result, noise from a variety of sources that may impact the performance of the MRI system may be detected and used to suppress and/or eliminate noise from MR signals detected by the MRI system during operation. Because techniques described herein operate on the particular noise environment of the MRI system, the noise suppression techniques described herein facilitate deployment of an MRI system wherever the system may be needed, eliminating the requirement that the system be installed in specially shielded rooms. The ability to dynamically adapt to changing noise environments facilitates development of MRI systems that can be deployed in generally noisy environments, including environments where noise sources may change over time. Because techniques described herein can be utilized during operation of the MRI system, the noise environment can be characterized dynamically so that it reflects the same noise environment to which the system is currently being exposed. When utilized in connection with a low-field MRI system, a cost effective, high availability and transportable MRI solution may be achieved in part using the noise suppression techniques described herein.

Having thus described several aspects and embodiments of the technology set forth in the disclosure, it is to be appreciated that various alterations, modifications, and improvements will readily occur to those skilled in the art. Such alterations, modifications, and improvements are intended to be within the spirit and scope of the technology described herein. For example, those of ordinary skill in the art will readily envision a variety of other means and/or structures for performing the function and/or obtaining the results and/or one or more of the advantages described herein, and each of such variations and/or modifications is deemed to be within the scope of the embodiments described herein. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, inventive embodiments may be practiced otherwise than as specifically described. In addition, any combination of two or more features, systems, articles, materials, kits, and/or methods described herein, if such features, systems, articles, materials, kits, and/or methods are not mutually inconsistent, is included within the scope of the present disclosure.

The above-described embodiments can be implemented in any of numerous ways. One or more aspects and embodiments of the present disclosure involving the performance of processes or methods may utilize program instructions executable by a device (e.g., a computer, a processor, or other device) to perform, or control performance of, the processes or methods. In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other tangible computer storage medium) encoded with one or more programs that, when executed on one or more computers or other processors, perform methods that implement one or more of the various embodiments described above. The computer readable medium or media can be transportable, such that the program or programs stored thereon can be loaded onto one or more different computers or other processors to implement various ones of the aspects described above. In some embodiments, computer readable media may be non-transitory media.

The terms "program" or "software" are used herein in a generic sense to refer to any type of computer code or set of computer-executable instructions that can be employed to program a computer or other processor to implement various aspects as described above. Additionally, it should be appreciated that according to one aspect, one or more computer programs that when executed perform methods of the present disclosure need not reside on a single computer or processor, but may be distributed in a modular fashion among a number of different computers or processors to implement various aspects of the present disclosure.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

The above-described embodiments of the present invention can be implemented in any of numerous ways. For example, the embodiments may be implemented using hardware, software or a combination thereof. When implemented in software, the software code can be executed on any suitable processor or collection of processors, whether provided in a single computer or distributed among multiple computers. It should be appreciated that any component or collection of components that perform the functions described above can be generically considered as a controller that controls the above-discussed function. A controller can be implemented in numerous ways, such as with dedicated hardware, or with general purpose hardware (e.g., one or more processor) that is programmed using microcode or software to perform the functions recited above, and may be implemented in a combination of ways when the controller corresponds to multiple components of a system.

Further, it should be appreciated that a computer may be embodied in any of a number of forms, such as a rack-mounted computer, a desktop computer, a laptop computer, or a tablet computer, as non-limiting examples. Additionally, a computer may be embedded in a device not generally regarded as a computer but with suitable processing capabilities, including a Personal Digital Assistant (PDA), a smartphone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible formats.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

Also, as described, some aspects may be embodied as one or more methods. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

What is claimed is:

1. A method of suppressing noise in an environment of a magnetic resonance imaging system, the method comprising:
    obtaining, using at least one primary coil and at least one auxiliary sensor different from the at least one primary coil, multiple calibration signals comprising a first plurality of calibration signals and a corresponding second plurality of calibration signals by:
        obtaining the first plurality of calibration signals using the at least one auxiliary sensor, wherein each of the first plurality of calibration signals comprises multiple values; and
        obtaining the second plurality of calibration signals using the at least one primary coil, wherein each of the second plurality of calibration signals comprises multiple values;
    weighting the multiple calibration signals to obtain multiple weighted calibration signals at least in part by:
        weighting at least some of the first plurality of calibration signals using a weighting function; and
        weighting at least some of the second plurality of calibration signals using the weighting function;
    estimating, using the multiple weighted calibration signals, a transform that, when applied to noise received by the at least one auxiliary sensor, provides an estimate of noise received by the at least one primary coil; and
    after estimating the transform:

receiving a magnetic resonance signal using the at least one primary coil;

receiving a noise signal using the at least one auxiliary sensor;

estimating noise present in the magnetic resonance signal received by the at least one primary coil by applying the transform to the noise signal received by the at least one auxiliary sensor to obtain a noise estimate; and suppressing noise in the magnetic resonance signal using the noise estimate.

2. The method of claim 1, wherein the weighting function is a Gaussian weighting function.

3. The method of claim 1, wherein the weighting function is a step weighting function or a linear weighting function.

4. The method of claim 1, wherein the weighting function is a k-space weighting function.

5. The method of claim 1, wherein obtaining the first plurality of calibration signals comprises obtaining at least ten calibration signals using the at least one auxiliary sensor.

6. The method of claim 1, wherein obtaining the first plurality of calibration signals comprises obtaining at least one hundred calibration signals using the at least one auxiliary sensor.

7. The method of claim 1, wherein the at least one primary coil is arranged within a field of view of the magnetic resonance imaging system to detect magnetic resonance signals produced by a sample when positioned within the field of view, and wherein the at least one auxiliary sensor comprises at least one auxiliary coil arranged outside the field of view.

8. The method of claim 1, wherein the noise signal is received by the at least one auxiliary sensor concurrently with the at least one primary coil receiving the magnetic resonance signal.

9. The method of claim 1, wherein each of the first plurality of calibration signals is obtained substantially at a same set of times as respective ones of the second plurality of calibration signals.

10. The method of claim 1, wherein estimating the transform includes estimating the transform for each of a plurality of frequency bins across a spectrum of interest.

11. The method of claim 1, wherein the magnetic resonance imaging system is a low-field magnetic resonance imaging system configured to generate a $B_0$ field having a strength between 0.05 T and 0.1 T.

12. The method of claim 1, wherein the magnetic resonance imaging system is a low-field magnetic resonance imaging system configured to generate a $B_0$ field having a strength between 0.1 T and 0.2 T.

13. A magnetic resonance imaging (MRI) system comprising:
at least one primary coil;
at least one auxiliary sensor different from the at least one primary coil; and
at least one controller configured to:
cause the at least one auxiliary sensor and the at least one primary coil to obtain a first plurality of calibration signals and a second plurality of calibration signals, respectively, from an environment of the magnetic resonance imaging system, wherein each of the first plurality of calibration signals includes multiple values and each of the second plurality of calibration signals includes multiple values;

weight at least some of the first plurality of calibration signals using a weighting function;

weight at least some of the second plurality of calibration signals using the weighting function;

estimate, based on the weighted first plurality of calibration signals and the weighted second plurality of calibration signals, a transform that, when applied to noise received by the at least one auxiliary sensor, provides an estimate of noise received by the at least one primary coil; and after estimating the transform:
cause the at least one primary coil to receive a magnetic resonance signal;
cause the at least one auxiliary sensor to receive a noise signal;
estimate noise present in the magnetic resonance signal received by the at least one primary coil by applying the transform to the noise signal received by the at least one auxiliary sensor to obtain a noise estimate; and
suppress noise in the magnetic resonance signal using the noise estimate.

14. The MRI system of claim 13, wherein the weighting function is a Gaussian weighting function.

15. The MRI system of claim 13, wherein each of the first plurality of calibration signals is a time series of values measured at a respective series of times using the at least one auxiliary sensor.

16. The MRI system of claim 13, wherein each of the second plurality of calibration signals is a time series of values measured at a respective series of times using the at least one primary coil.

17. The MRI system of claim 13, wherein causing the at least one auxiliary sensor to obtain the first plurality of calibration signals comprises causing the at least one auxiliary sensor to obtain at least one hundred calibration signals.

18. The MRI system of claim 13, wherein the at least one primary coil is arranged within a field of view of the MRI system to detect magnetic resonance signals produced by a sample when positioned within the field of view, and wherein the at least one auxiliary sensor comprises at least one auxiliary coil arranged outside the field of view.

19. The MRI system of claim 13, wherein the at least one controller causes the at least one auxiliary sensor to receive the noise signal and the at least one primary coil to receive the magnetic resonance signal at substantially a same time.

20. The MRI system of claim 13, wherein the at least one auxiliary sensor includes at least one auxiliary radio frequency coil.

* * * * *